(12) United States Patent
Santi et al.

(10) Patent No.: US 6,211,110 B1
(45) Date of Patent: Apr. 3, 2001

(54) BRIDGED METALLOCENE COMPLEX FOR THE (CO)POLYMERIZATION OF OLEFINS

(75) Inventors: Roberto Santi; Giampietro Borsotti; Gianfranco Longhini, all of Novara; Paolo Biagini, Trecate; Antonio Proto, Novara; Francesco Masi, Lodi; Viviano Banzi, Vigarano Mainarda, all of (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/262,318

(22) Filed: Mar. 4, 1999

(30) Foreign Application Priority Data

Mar. 10, 1998 (IT) .............................. MI98A0479

(51) Int. Cl.$^7$ .............. B01J 21/00; B01J 21/06
(52) U.S. Cl. ............ 502/152; 502/117; 502/154; 502/155; 526/127; 526/153; 526/160; 526/943
(58) Field of Search .................... 502/117, 152, 502/154, 155; 526/127, 153, 160, 943

(56) References Cited

U.S. PATENT DOCUMENTS

| | | | |
|---|---|---|---|
| 5,635,437 | * 6/1997 | Burkhardt et al. | 502/104 |
| 5,753,578 | 5/1998 | Santi et al. | 502/114 |
| 6,087,515 | * 7/2000 | Eisch et al. | 556/52 |

\* cited by examiner

*Primary Examiner*—Mark L. Bell
*Assistant Examiner*—Michael J. Di Verdi
(74) *Attorney, Agent, or Firm*—Oblon, Spivak, McClelland, Maier & Neustadt, P.C.

(57) ABSTRACT

A "bridged" bis-cyclopentadienyl complex which can be advantageously used for the formation of a catalytic system active in the (co)polymerization of ethylene and other α-olefins is represented by means of the following formula (II):

(II)

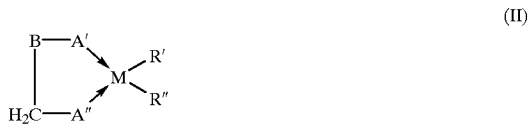

wherein: M represents a metal selected from titanium, zirconium or hafnium; A' and A" each independently represent an anion containing an $\eta^5$-cyclopentadienyl ring coordinated to M; R' or R" each independently represents a group of an anionic nature a-bound to the metal M; B represents an unsaturated bivalent organic residue having from 1 to 30 carbon atoms, bound, respectively, to the ring of group A' and to the —$CH_2$— methylene group by means of carbon atoms. This complex, combined with a suitable cocatalyst, forms a catalyst with a high activity in the polymerization of olefins, producing polymers with a high molecular weight, especially in the case of the copolymerization of ethylene with a second α-olefin.

20 Claims, 4 Drawing Sheets

BRIDGED METALLOCENE COMPLEX FOR THE (CO)POLYMERIZATION OF OLEFINS

BACKGROUND OF THE INVENTION

1. Field of the Invention

The present invention relates to a bridged metallocene complex which can be used for the (co)polymerization of olefins.

More specifically, the present invention relates to a particular bridged metallocene complex of a transition metal, in addition to a catalyst comprising said complex, or deriving therefrom, suitable for the polymerization or copolymerization of ethylene and other α-olefins, optionally combined with a suitable cocatalyst. The present invention also relates to a method for the preparation of said metallocene complex and the corresponding ligands, as well as a polymerization process of olefins using this.

2. Discussion of the Background

It is generally known in the art that ethylene, or α-olefins in general, can be polymerized or copolymerized by means of processes at low, medium or high pressure with catalysts based on a transition metal, generally known as catalysts of the Ziegler-Natta type. A particular group of catalysts active in the polymerization of olefins consists of a combination of an organic oxyderivative of aluminum (in particular, polymeric methyl-aluminoxane or MAO) with an $\eta^5$-cyclopentadienyl derivative (metallocene) of a transition metal of groups 3 to 6 of the periodic table of elements (in the form approved by IUPAC and published by "CRC Press Inc." in 1989). Particularly interesting results have been obtained with catalysts based on metallocenes of group 4, i.e. which can be defined, in their more general form, by the following formula (I):

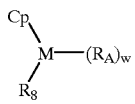

(I)

wherein M represents a metal of group 4; each $R_A$ independently represents a group of an anionic nature such as, for example, a hydride, a halide, a phosphonate or sulfonate anion, an alkyl or alkoxy group, an aryl or aryloxy group, an amide group, a silyl group, etc.; "w" is an index that can be an integer 1 or 2 depending on whether the valence of M is 3 or 4; Cp represents a ligand of the $\eta^5$-cyclopentadienyl type and is generally selected from $\eta^5$-cyclopentadienyl, $\eta^5$-indenyl, $\eta^5$-fluorenyl groups or a substituted derivative of these; $R_B$ may, regardless of the nature of the other substituents, have one of the definitions of either the ligand Cp, or $R_A$ groups. So-called "bridged" metallocenes have also proved to be of particular interest in the known art, wherein two Cp groups, the same or different, are coordinated to the metal M and covalently bound to each other by means of a bivalent organic group. For a known method for the preparation of the above compounds, reference should be made to the description of H. Sinn, W. Kaminsky, in. Adv. Organomet. Chem., vol. 18 (1980), page 99 and U.S. Pat. No. 4,542,199.

These catalysts generally have a high catalytic activity and a certain versatility when applied to the preparation of polyolefins with specific characteristics, especially with respect to the stereochemical control of the polymerization of α-olefins such as propylene.

The introduction of a "bridged" group, in particular, allows the two pentahapto-coordinated rings ($\eta^5$) of the cyclopentadienyl ligand to be kept in a stricter reciprocal position than when the bridge is absent. This modification enables the production of polymers with specific characteristics, at times impossible to obtain with non-bridged metallocenes, depending on the catalytic composition and olefin to be polymerized.

It is known that certain "bridged" metallocene catalysts are capable of polymerizing α-olefins with a high stereospecificity. Whereas the complex (Ind)$_2$ZrCl$_2$ provides a polypropylene with a low isotacticity index [L. Resconi et al. Macromolecules 25, 6814–6817, (1992)], the corresponding catalysts with ethylidene and dimethylsilyl bridges (in the racemic isomeric form) give polypropylene with an isotacticity of 99% and 97% respectively, as described for example in German patents DE 3.743.321 and DE 3.443.087.

In the publication EP-A 310.734, at least two of the above complexes having formula (I) are mixed with each other to obtain a polymer with an enlarged molecular weight distribution (MWD>3) and which is therefore more easily processable in an extruder. "Makromoleculare Chemie", vol. 194 (1993), pages 1745–1755, describes "bridged" complexes supported on inorganic substrates (Al$_2$O$_3$ MgCl$_2$) and used in the presence of trialkylaluminum AlR$_3$, instead of MAO, in the polymerization of propylene, whereas in patent application EP-A 418-044 cationic "bridged" complexes are used, which are active in polymerization even without MAO.

Patent and scientific literature on "bridged" catalysts is very broad. The numerous structures studied and claimed are preferably based on Zr and Hf and contain, as pentahapto-coordinated ligands, cyclopentadienyl (Cp), indenyl (Ind) or fluorenyl (Flu) rings, optionally substituted with appropriate groups in certain positions of the molecular skeleton, in order to improve the performance of the catalyst and resulting polymer. For example, W. Spaleck et al., in "Angewandte Chemie, Int. Ed. Eng." vol. 31 (1992), pages 1347–1349, state that the catalyst Me$_2$Si(Ind)$_2$ZrCl$_2$ allows the production of a polypropylene with a higher molecular weight if a methyl substituent is placed in position 2 on the indenyl ring, whereas, according to "Organometallics", vol. 13 (1994), pages 954–963, a further substitution with a naphthoic group in position 4, also increases the yield to polymer and tacticity index.

Numerous other examples are cited in patent literature, for example in European patent applications EP-A 582.194, EP-A 537.130, EP-A 574.370 and EP-A 581.754.

In spite of the many advantages with respect to the prior known art, represented by the so-called "classical" Ziegler-Natta catalysts, having an intrinsically heterogeneous and multicentric nature, catalysts based on metallocenes also have various disadvantages however, such as, for example, the production of polymers with an average molecular weight which is still insufficient, especially with polymerization processes at high temperatures. In addition, also in the case of metallocenes, it is desirable to further improve the stereoselectivity in the polymerization of α-olefins with processes at a high temperature and pressure, of about 150–250° C. and 50–100 MPa. It would also be preferable to further increase the activation and polymerization rate provided by the catalytic system in processes characterized by reduced residence times in the reactor.

Another rather unsatisfactory aspect of the above catalysts relates to their behaviour in the copolymerization of ethylene to produce low density polyethylene or olefinic elastomers, again with respect to the difficulty in obtaining copolymers with sufficiently high molecular weights, suitable for their numerous industrial applications. It is known, in fact, that it is necessary to operate with significant quantities of comonomer to insert the desired quantity into the copolymer, with a consequent increase in the rate of the chain transfer reaction, competitive with the polymerization, and the production of unsatisfactory molecular weights. This disadvantage becomes even more critical when operating with polymerization processes at a high temperature in which the chain transfer reaction is already substantial without the comonomer. Not less significant, in this respect, is the quantity of comonomer inserted, as well as the "means" of insertion, referring to the formation of comonomer block sequences, rather than a more desirable statistic distribution.

Although different types of variously substituted $\eta^5$-cyclopentadienyl ligands have been studied in detail in the known art in order to overcome the above disadvantages and improve the characteristics according to the specific applications, there are few publications on the influence, in a polymerization process, of groups forming the "bridge" between these ligands, which are basically limited, in practice, to the groups —$CH_2$—$CH_2$—, —$CMe_2$—, and —$Si(R_CR_D)$— (being $R_C$ and $R_D$ alkyl or aryl groups).

The publication "Makromolekulare Chemie, Rapid Comm.", Vol. 14 (1993), pages 633–636, describes particular polymerization catalysts based on bis-($\eta^5$-cyclopentadienyl) complexes containing a bridge between the two ligands consisting of a 1,3-phenylenedimethylene group. These complexes, although capable of polymerizing ethylene in the presence of MAO, have poor solubility in aromatic and/or aliphatic hydrocarbons, and a much lower activity than that of the commoner metallocene complexes, such as, for example $(\eta^5-C_5H_5)_2ZrCl_2$.

The publication "Acta Chimica Sinica", vol. 48 (1990), pages 298–301, describes the preparation of some zirconium and titanium bis-cyclopentadienyl complexes, which contain a phenylenedimethylene bridge between the two cyclopentadienyl ligands. No mention is made, however, in this publication of the possible use of these complexes in the polymerization of olefins.

European patent application EP-A 752.428, filed by the Applicant, discloses bridged metallocene complexes in which the two $\eta^5$-cyclopentadienyl groups are bridge-bound with a divalent group having the formula —$CH_2$—(A)—$CH_2$—, wherein A is a divalent unsaturated hydrocarbon group. Although these complexes allow a reasonable reaction rate to be reached in the formation of olefinic homo- and copolymers, their insertion capacity of the comonomer in the copolymerization of ethylene, is still unsatisfactory.

SUMMARY OF THE INVENTION

The Applicant has now found a new group of metallocene complexes containing particular "bridged" groups, which in the presence of a suitable cocatalyst, are capable of catalyzing the (co)polymerization of $\alpha$-olefins without the drawbacks mentioned above and giving a polymer with a high yield and molecular weight.

A first object of the present invention therefore relates to a metallocene complex having the following formula (II):

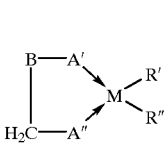

(II)

wherein: M represents a metal selected from titanium, zirconium or hafnium;
  each A' or A" independently represents an organic group cntaining an $\eta^5$-cyclopentadienyl ring of an anionic nature, coordinated to the metal M;
  each R' or R" independently represents a group of an anionic nature a-bound to the metal M; preferably selected from hydride, halide, a $C_1$–$C_2$ alkyl or alkylaryl group, a $C_3$–$C_{20}$ alkylsilyl group, a $C_5$–$C_{20}$ cycloalkyl group, a $C_6$–$C_{20}$ aryl or arylalkyl group, a $C_1$–$C_{20}$ alkoxyl or thioalkoxyl group, a $C_2$–$C_{20}$ carboxylate or carbamate group, a $C_2$–$C_{20}$ dialkylamide group and a $C_4$–$C_{20}$ alkylsilylamide group;
  B represents an unsaturated divalent organic residue having from 1 to 30 carbon atoms, bound, respectively, to the cyclopentadienyl ring of group A' and to the —$CH_2$— methylene group by means of unsaturated atoms different from hydrogen.

A second object of the present invention relates to a process for the (co)polymerization of olefins, comprising polymerzing or copolymerizing ethylene and/or one or more $\alpha$-olefins, under suitable conditions of pressure and temperature, in the presence of a catalyst obtained from the combination (contact and reaction) of the above metallocene complex with a suitable activator (or cocatalyst) selected from those known in the art, particularly an organic compound of a metal M' selected from boron, aluminum, gallium and tin, or a combination of these compounds.

Other possible objects of the present invention will appear evident from the following description and examples.

BRIEF DESCRIPTION OF THE DRAWINGS

The invention will be described in detail with reference to the following figures, wherein.

DETAILED DESCRIPTION OF THE INVENTION

Figure 1:
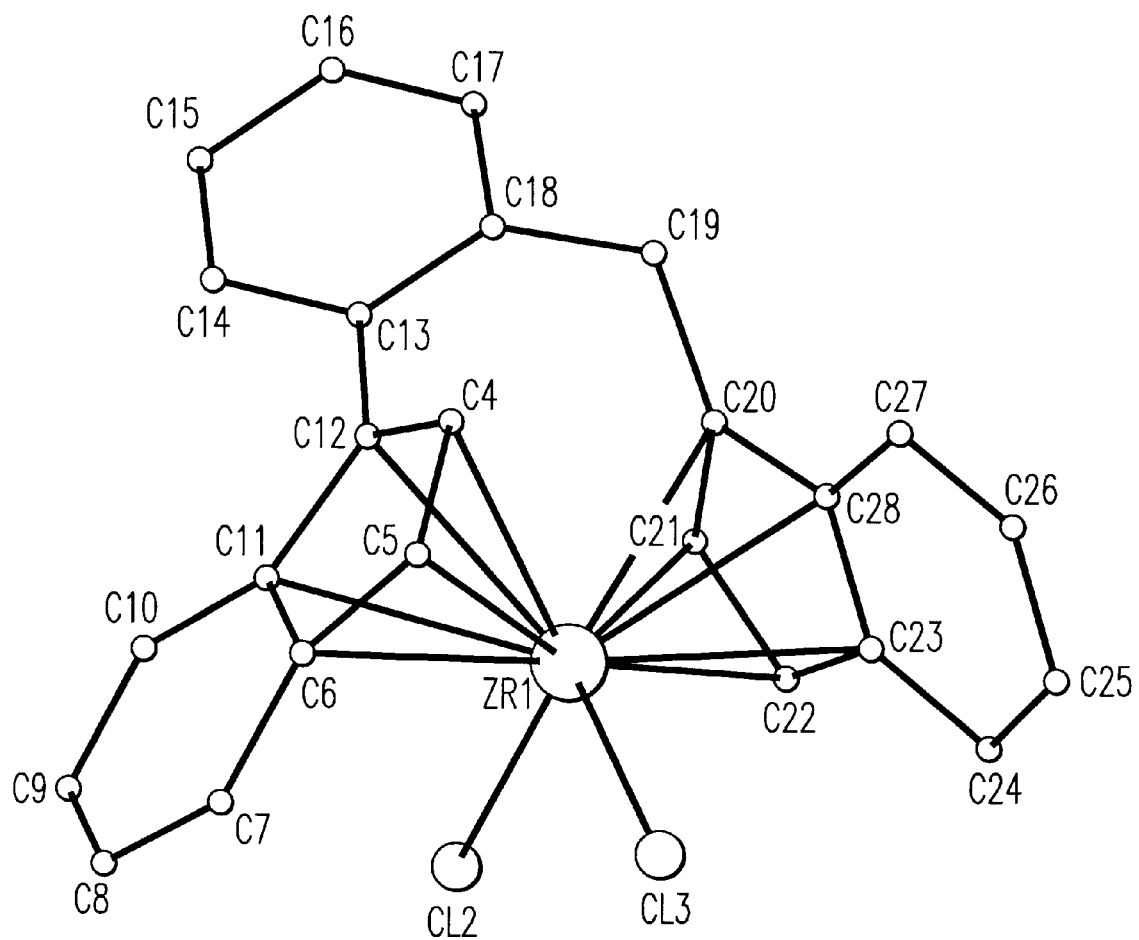
FIG. 1 is the X-ray structure of the complex having formula (VIII)

The term "unsaturated atom", as used in the present invention and claims, refers to atoms of an organic or organometallic compound, which form a double bond, of the olefinic or aromatic type, with at least one other atom.

In the complexes having formula (II) of the catalysts of the present invention, the —B—$CH_2$— group bridge-joins the two cyclopentadienyl groups A' and A" giving the molecular structure a specific geometry, deriving from the intrinsic asymmetry of the "bridge", and the fact that this B group is bound to the rest of the structure -having formula (II) by means of bonds adjacent to an unsaturated bond. This generally consists of a cyclic or acyclic, unsaturated organic group, containing from 1 to 30 carbon atoms, which may also comprise one or more non-metallic heteroatoms included in groups 14 to 17 of the periodic table of elements, preferably selected from Si, N, O, S, P, Cl, Br and F, more preferably from Si, N, O and F. In a particular embodiment the B group is a $C_2$–$C_{20}$ unsaturated hydrocarbyl group not containing heteroatoms.

This unsaturated B group can be an olefinically unsaturated group characterized by a double bond such as, for example, a —C=C— vinylidene group, or a —C=N— group containing a heteroatom. This olefinically unsaturated group can be bound to groups —A'— and —CH$_2$—A"— respectively of the complex having formula (II) with the two atoms at the ends of the double bond, with a "Z" configuration, such as, for example, in the following "bridged" groups:

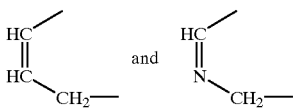

or it may comprise a single carbon atom bound to both of the above groups, such as for example in the case of B groups having the following formulae:

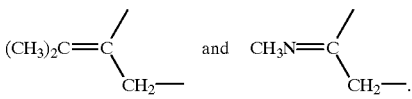

Group B of the present invention may also consist of a phenylene group, preferably ortho-phenylene, optionally substituted on any of the remaining positions of the ring. Typical substituent groups are those which are compatible with the use of the complex having formula (II) in the polymerization catalysis of olefins, i.e. groups which do not react with the cocatalysts as defined hereunder. Examples of these substituent groups are halogen, such as fluorine, chlorine or bromine, a $C_1$–$C_{10}$ alkyl group such as, for example, methyl, ethyl, butyl, isopropyl, isoamyl, octyl, benzyl, a $C_3$–$C_{12}$ alkylsilyl group such as, for example, trimethylsilyl, triethylsilyl or tributylsilyl, a cycloalkyl group such as cyclopentyl or cyclohexyl, a $C_6$–$C_{10}$ aryl group such as phenyl or toluene, a $C_{1-C8}$ alkoxyl group such as, for example, methoxyl, ethoxyl, iso- or sec-butoxyl, or also groups forming an additional saturated or unsaturated condensed cycle with the main ring. Specific but non-limiting examples of phenylene B groups are o-phenylene, 2,5-dimethyl-o-phenylene, 3,4-dimethyl-o-phenylene, 3-ethyl-o-phenylene, 3-octyl-o-phenylene, 3,4-difluoro-o-phenylene, 2-methoxy-o-phenylene, m-phenylene, 4,6-dimethyl-m-phenylene, 5-phenyl-m-phenylene, 1,2-naphthylene, 2,3-naphthylene, 1,3-naphthylene, 2,3-phenanthrylene, etc.

A further category of divalent B groups included in the scope of the present invention consists of condensed aromatic groups in which the atoms bound to the two —A'— and —CH$_2$—A"— groups having formula (II) are in "peri" position on two adjacent aromatic rings. Groups belonging to this category are, for example, 1,8-naphthalene, 4,5-dimethyl-1,8-naphthalene, 5,6-acenaphthylene, etc.

According to the present invention, the groups R' and R" having formula (II) each independently represent a group of an anionic nature a-bound to the metal M. Typical examples of R' and R" are hydride, halide, preferably choride or bromide, a linear or branched alkyl group such as methyl, ethyl, butyl, isopropyl, isoamyl, octyl, decyl, benzyl, an alkylsilyl group such as, for example, trimethylsilyl, triethylsilyl or tributylsilyl, a cycloalkyl group such as cyclopentyl, cyclohexyl, 4-methylcyclohexyl, an aryl group such as phenyl or toluene, an alkoxyl group such as methoxyl, ethoxyl, iso- or sec-butoxyl, ethylsulfide, a carboxylate group such as acetate, trifluoroacetate, propionate, butyrate, pivalate, stearate, benzoate or a dialkylamide group such as diethylamide, dibutylamide, or an alkylsilylamide group, such as bis(trimethylsilyl)amide or ethyltrimethylsilylamide. The two groups R' and R" may also be chemically bound to each other and form a cycle having from 4 to 7 atoms different from hydrogen, also comprising the metal M. Typical examples of this aspect are divalent anionic groups such as the trimethylene or tetramethylene group or ethylenedioxy group. Particularly preferred R' and R" groups for their availability and the easy preparation of the complexes which contain them, are chloride, methyl and ethyl.

According to the present invention, each A' or A" group of an anionic nature in formula (II) contains an $\eta^5$-cyclopentadienyl ring coordinated to the metal M, which is formally derived from a substituted or non-substituted, cyclopentadienyl molecule, by the extraction of an H$^+$ ion. The molecular structure and typical electronic and coordinative configuration of metallocene complexes of titanium, zironcium or hafnium generally comprising two $\eta^5$-cyclopentadienyl groups has been widely described in literature and is known to experts in the field.

In the more general embodiment of the present invention, the —B—CH$_2$— "bridge" in formula (II) may be bound to any of the carbon atoms of the cyclopentadienyl ring of groups A' and A" respectively (provided a bond valence is available), preferably in position 1 or 3, when A' and/or A" consist of condensed bicyclic groups, such as, for example, indenyl or tetrahydroindenyl.

Each A' or A" group of the above preferred complexes is typically represented by the following formula (III):

wherein each substituent $R_1$, $R_2$ $R_3$ and $R_4$ independently represents hydrogen, halogen, preferably F, Cl or Br, an aliphatic or aromatic $C_1$–$C_{20}$ hydrocarbyl group, optionally comprising one or more heteroatoms different from carbon and hydrogen, especially F, Cl, O, S and Si, or, wherein at least any two of the substituents $R_1$, $R_2$, $R_3$ and $R_4$, adjacent to each other, are joined to each other to form a saturated or unsaturated $C_4$–$C_{20}$ cyclic structure, comprising a bond of the cyclopentadienyl ring, said structure optionally containing one or more of the heteroatoms specified above.

Included in the above formula (III) of preferred groups A' or A" are the known cyclopentadienyl, indenyl or fluorenyl groups, and their homologous products, wherein one or more carbon atoms of the molecular skeleton (with or without the cyclopentadienyl ring), are substituted with halogen, preferably chlorine or bromine, a linear or branched alkyl group such as methyl, ethyl, butyl, isopropyl, isoamyl, octyl, decyl, benzyl, an alkylsilyl group such as, for example, trimethylsilyl, triethylsilyl or tributylsilyl, a cycloalkyl group such as cyclopentyl, cyclohexyl, 4-methylcyclohexyl, an aryl group such as phenyl or toluene, an alkoxyl or thioalkoxyl group such as methoxyl, ethoxyl, iso- or sec-butoxyl, ethylsulfide, a dialkylamide group such as diethylamide, dibutylamide, or an alkylsilylamide group, such as bis(trimethylsilyl)amide or ethyltrimethylsilylamide. These A' or A" groups may also comprise several condensed aromatic rings, as in the case, for example, of 4,5-benzoindenyl. Particularly preferred A' or A" groups are cyclopentadienyl, indenyl, 4,5,6,7-tetrahydroindenyl, fluorenyl groups and the corresponding methylsubstituted groups.

Typical examples of complexes having formula (II) which are suitable for the purposes of the present invention are the following compounds, which however in no way limit the overall scope of the present invention.

1,3-propenylidene-(1-Ind)$_2$ZrCl$_2$;
1,3-propenylidene-(1-Ind) $_2$TiCl$_2$;
1,8-Naphth-(1-Ind) $_2$ZrCl$_2$;
1,8-Naphth-(1-Ind)$_2$Zr(NMe$_2$)$_2$;
o-benzylidene-[1(3-methyl) Ind]$_2$HfCl$_2$;
o-benzylidene-(1-Ind)$_2$ZrCl$_2$ ;
o-benzylidene-(Flu)$_2$HfCl;
o-benzylidene-(1-Ind)$_2$TiC$_{12}$ ;
o-benzylidene-(Flu)$_2$ZrBz$_2$;
o-benzylidene-(C$_5$H$_4$) 2Zr (OCOCMe$_3$)$_2$;
o-benzylidene-(1-nd) $_2$Zr (OCO-CF$_3$)$_2$;
o-benzylidene-[(5,6-dimethyl)Ind]$_2$ZrCl$_2$;
o-benzylidene-[1-(4,7-dimethyl) Ind]$_2$TiBr$_2$;
o-benzylidene-[1-(4,7-diphenyl) Ind]$_2$ZrMe$_2$;
o-benzylidene-[1-(4,5,6,7-THInd)$_2$TiCl$_2$;
o-benzylidene-[1-(3-methyl) Ind] $_2$ TiCl$_2$;
o-benzylidene-[1-(3,4,7-trimethyl)Ind]$_2$ZrCl$_2$;
o-benzylidene-[3-(5, 1-dimethyl) Ind] $_2$ZrMe$_2$;
(Flu-o-benzylidene-Cp*)Ti (NMe$_2$)$_2$;
o-benzylidene-[1-(4,7-dimethyl) md]$_2$TiBz$_2$;
o-benzylidene-(1-Ind)$_2$Zr(OCO—n—C$_3$H$_7$)$_2$.

The following abbreviations were used in the above formulae: 1,8-Naphth=1,8-naphthalidenemethylidene, Me=methyl, Bz=benzyl, Ind=indenyl, Flu=fluorenyl, THInd=4,5,6,7-tetrahydroindenyl, Cp=tetramethylcyclopentadienyl.

The preparation of the above complexes having formula (II) can be effected with one of the known methods described in literature for the production of "bridged" bis-cyclopentadienyl complexes of transition metals, obviously modifying the methods to adapt them to the production of the desired complex.

The most commonly used method comprises reacting a salt of the metal M (preferably a chloride), with a salt of an alkaline metal with the dianion of the bis-cyclopentadienyl ligand having the desired structure. In the more general case, this ligand has the general formula (IV):

wherein A', A" and B all have the general meaning previously specified for complexes represented by formula (II), with the obvious difference that, in this case, each cyclopentadienyl group A' or A" is not $\eta^5$-coordinated with the metal M, and is not of an aromatic nature, but is a neutral radical with the adjacent hydrogen atom as represented in formula (IV).

The above radicals —A'H and HA"— preferably have a structure that can be schematically represented by the following formula (IV-bis):

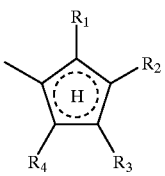

wherein: each substituent R$_1$, R$_2$, R$_3$ and R$_4$ has the same meaning and the same preference criteria as the corresponding group R$_i$ (i=1, 2, 3 or 4) in formula (III)
  the hydrogen atom represented at the centre of the cycle is indifferently bound to any of the carbon atoms of the cyclopentadienyl ring, and
  the dotted circle schematically represents the two double conjugated bonds on the remaining four atoms of the cyclopentadienyl ring.

Typical, non-limiting examples of compounds having formula (IV) according to the present invention are 1-(1-indenyl)-2-(1-indenyl)methylbenzene, 1-[1-(4,5,6,7-tetrahydro)indenyl]-2-(1-indenyl)methylbenzene, 1-[1-(4,5, 6, 7-tetrahydro) indenyl]-2-(1-(4,5,6, 7-tetrahydro)-indenyl] methylbenzene, 1-(4,7-dimethyl-1-indenyl)-2-(4,7-dimethyl-1-indenyl)methyl-benzene, 1-(cyclopentadienyl)-2-(cyclopentadienyl)methylbenzene, 1-(1-indenyl)-8-(1-indenyl)methylnaphthalene.

The preparation of the complexes having formula (II) normally comprises two steps, in the first of which the ligand having formula (IV) is reacted with a lithiumalkyl, such as lithium-methyl or lithiumbutyl, or a corresponding magnesium derivative, in an inert solvent preferably consisting of an aromatic hydrocarbon or an ether, particularly tetrahydrofuran or ethyl ether. The temperature during the reaction is preferably maintained below room temperature to avoid the production of secondary reactions. At the end of the reaction the corresponding lithium salt of the cyclopentadienyl dianion is obtained.

In the second step, the salt of the cyclopentadienyl dianion is reacted with a salt, preferably a chloride, of the transition metal M, again in an inert organic solvent and a temperature preferably below room temperature, normally between −50 and 0° C. At the end of the reaction the complex having formula (II) thus obtained is separated and purified according to the known methods of organometallic chemistry. As known to experts in the fields, the above operations are sensitive in the presence of air and must be carried out in an inert atmosphere, preferably under nitrogen or argon.

Numerous methods, both general and specific, are described in literature basically analogous to the method described above, such as, for example, in the publications of D. J. Cardin "Chemistry of Organo Zr and Hf compounds" J. Wiley and Sons Ed., New York (1986); R. Halterman "Chemical Review", vol. 92 (1992) pages 965–994; R. O. Duthaler and A. Hafner "Chemical Review", vol. 92 (1992) pages 807–832.

The Applicant has also found an original synthetic process for the preparation of a particular group of bis-cyclopentadienyl ligands included in formula (IV), in which the "bridge" B consists of an ortho-phenylene group and the group Al is different from fluorene or fluorene substituted. This process, which forms another object of the present invention, allows the above ligands to be obtained with satisfactory yields and a high purity, and it also makes those ligands whose A' and A" groups have a different structure (asymmetrical), easily accessible.

In accordance with what is specified above, a further object of the present invention relates to a method for the preparation of a compound having the following formula (V):

$$HA''—CH_2—B'—A'H \quad (V)$$

wherein: each —A'H or HA''— radical independently represents a cyclopentadienyl group included in the previous formula (IV-bis), on the condition that A'H is different from fluorenyl or fluorenyl substituted, and B represents a divalent organic radical having from 6 to 30 carbon atoms and comprising a benzene aromatic ring, whose two valences are in position ortho (adjacent to each other) on said aromatic ring, characterized in that it comprises the following steps in succession:

a) protection of the alcohol group of an o-bromobenzylalcohol having the formula HO—CH$_2$—B'—Br, wherein B' is defined as above, by reaction, with an enol-alkylether R$^6$—O—CR$^7$=CH having from 3 to 10 carbon atoms, with R$^6$=C$_1$–C$_6$ alkyl and R$^7$=hydrogen or C$_1$–C$_6$ alkyl, for example, 2-methoxypropene, in the presence of a catalytic quantity of an aprotic Lewis acid, preferably POCl$_3$, with the formation of the corresponding gem-diether Br—B'—CH—H—CR$^7$(CH$_3$)—O—R$^6$;

b) metallation of the gem-diether obtained according to step (a) with an alkyl compound of lithium or magnesium having from 1 to 10 carbon atoms, for example butyllithium or diethylmagnesium, in apolar solvents at a temperature ranging from 0 to 30° C., obtaining the corresponding lithium or magnesium salt, (Li or Mg)—B'—CH$_2$—O—CR$^7$(CH$_3$)—O—R$^6$ by substitution of the bromine atom;

c) condensation of the salt thus obtained with a precursor of the —A'H group consisting of a cyclopentenone having the corresponding structure, wherein the carbonyl oxygen is on the carbon in the cycle position which must be bound to said magnesium or lithium salt, for example 1-indanones or 2-indanones, in THF at a temperature lower than –30° C., preferably between –50 and –100° C., followed by hydrolysis of the reaction mixture and elimination of water obtaining the compound having the following formula (V-bis):

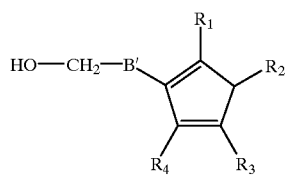

(V-bis)

or, preferably, of the corresponding bicyclic spiroderivative by addition of the —OH group to the double bond in position alpha with respect to B';

wherein the various symbols B', R$_1$, R$_2$, R$_3$ and R$_4$ all have the meaning defined above;

d) reaction of the compound having formula (V-bis), or the corresponding spiro derivative, obtained as in step (c), with aqueous hydrochloric or hydrobromic acid in excess, preferably a concentrated solution of HBr (>25% by weight), at a temperature ranging from 50° C. to 130° C., preferably at the reflux temperature of the mixture, to form an ortho-cyclpentadienylbenzyl halide having the same structure as the compound having formula (V-bis), with the only difference that the —OH group is substituted with the corresponding —Cl or —Br, preferably Br, halide;

e) contact and reaction of the cyclopentadienylbenzyl halide obtained as in step (d) with an organometallic compound of lithium or magnesium having the formula HA''(Li or MgR$^8$), with A'' having the same meaning as the previous formula (V) and R$^8$ selected from Cl, Br or A'', for example indenyl, fluorenyl or cyclopentadienyl lithium as such or variously substituted, in a suitable solvent, preferably a mixture of THF/hexane, at a temperature ranging from 10 to 40° C., to form the desired ligand.

A further aspect of the present invention therefore relates to a catalyst for the (co)polymerization of ethylene and other α-olefins, i.e. for the homopolymerization of ethylene and other α-olefins, the copolymerization of ethylene with one or more other copolymerizable monomers such as, for example, α-olefins, conjugated or non-conjugated diolefins, derivatives of styrene, etc., the copolymerization of α-olefins with each other or with other monomers copolymerizable with them. This catalyst comprises, or is obtained by contact and reaction of, at least the following two components:

(i) at least one metallocene complex having formula (II), and
(ii) a cocatalyst consisting of at least one organic compound of an element M' different from carbon and selected from the elements of groups 2, 12, 13 or 14 of the periodic table as previously defined.

In particular, according to the present invention, said element M' is selected from boron, aluminum, zinc, magnesium, gallium and tin, more particularly boron and aluminum.

In a preferred embodiment of the present invention, component (ii) is an organo-oxygenated derivative of aluminum, gallium or tin. This can be defined as an organic compound of M', wherein the latter is bound to at least one oxygen atom and at least one organic group consisting of an alkyl group having from 1 to 6 carbon atoms, preferably methyl.

According to this aspect of the present invention, component (ii) is more preferably an aluminoxane. As is known, aluminoxanes are compounds containing Al—O—Al bonds, with a varying O/Al ratio, which can be obtained in the art by reaction, under controlled conditions, of an aluminum alkyl, or aluminum alkyl halide, with water or other compounds containing pre-established quantities of available water, as for example, in the case of the reaction of aluminum trimethyl with aluminum sulfate hexahydrate, copper sulfate pentahydrate or iron sulfate pentahydrate. Aluminoxanes preferably used for the formation of the polymerization catalyst of the present invention are oligo- or poly-meric, cyclic and/or linear, compounds characterized by the presence of repetitive units having the following formula:

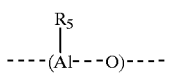

wherein R$_5$ is a C$_1$–C$_6$ alkyl group, preferably methyl.

Each aluminoxane molecule preferably contains from 4 to 70 repetitive units which are not necessarily equal to each other, but can contain different R$_5$ groups.

These aluminoxanes, and particularly methylaluminoxane, are compounds which can be obtained with known processes of organometallic chemistry, for example by the addition of aluminum trimethyl to a suspension in hexane of aluminum sulfate hydrate.

When used for the formation of a polymerization catalyst of the present invention, the aluminoxanes are put in contact with a complex having formula (II) in such proportions that the atomic ratio between Al and the metal M is within the range of 10 to 10000 and preferably between 100 and 5000. The sequence with which the complex (i) and the aluminoxane (ii) are put in contact with each other, is not critical.

In addition to the above aluminoxanes, galloxanes (in which gallium is present instead of aluminum in the above formulae) and stannoxanes are also included in the definition of component (ii) of the present invention, whose use as cocatalysts in the copolymerization of olefins in the presence of metallocene complexes is disclosed, for example, in patents U.S. Pat. No. 5,128,295 and U.S. Pat. No. 5,258,475.

According to another preferred embodiment of the present invention, said catalyst can be obtained by putting component (i) consisting of at least one complex having formula (II), in contact with component (ii) consisting of at least one compound or a mixture of organometallic compounds of M' capable of reacting with the complex having formula (II) extracting an σ-bound R' or R" group from this to form on the one hand at least one neutral compound, and on the other hand an ionic compound consisting of a metallocene cation containing the metal M and a non-coordinating organic anion containing the metal M', whose negative charge is delocalized on a multicentric structure.

Components (ii) suitable as ionizing systems of the above type are preferably selected from voluminous organic compounds of boron and aluminum, such as, for example, those represented by the following general formulae:

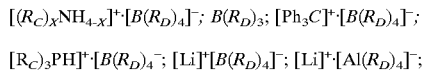

wherein the subscript "x" is an integer between 0 and 3, each $R_C$ group independently represents an alkyl or aryl radical having from 1 to 10 carbon atoms and each $R_D$ group independently represents an aryl radical partially, or even better, totally fluorinated, having from 6 to 20 carbon atoms.

These compounds are generally used in such quantities that the ratio between the atom MI in component (ii) and the atom M in the metallocene complex is within the range of 0.1 to 15, preferably form 0.5 to 10, more preferably from 1 to 6.

Component (ii) may consist of a single compound, normally an ionic compound, or a combination of this compound with MAO, or, preferably, with an aluminum trialkyl having from 1 to 8 carbon atoms in each alkyl residue, such as, for example, $AlMe_3$, $AlEt_3$, $Al(i\text{-}Bu)_3$.

In general, the formation of the ionic metallocene catalyst of the present invention is preferably carried out in an inert liquid medium, more preferably hydrocarbon. The selection of components (i) and (ii) which are preferably combined with each other, as well as the specific method used, can vary in relation to the molecular structure and desired result, according to what is amply described in specific literature available to experts in the art.

Examples of these methods are qualitatively schematized in the following list which, however, in no way limits the scope of the present invention:

($m_1$) by contact of a metallocene having the above formula (II) in which at least one, and preferably both, of the substituents R' and R" is hydrogen or an alkyl radical, with an ionic compound whose cation is capable of reacting with one of said substituents to form a neutral compound, and whose anion is bulky, non-coordinating and capable of delocalizing the negative charge;

($m_2$) by reaction of a metallocene having the above formula (II) with an alkylating agent, preferably an aluminum trialkyl, used in molar excess ranging from 10/1 to 300/1, followed by reaction with a strong Lewis acid, such as, for example, tris(pentafluorophenyl) boron in practically stoichiometric quantities or in slight excess with respect to the metal M;

($m_3$) by contact and reaction of a metallocene having the above formula (II) with a molar excess ranging from 10/1 to 1000/1, preferably from 100/1 to 500/1 of an aluminum trialkyl or an alkylaluminum halide which can be represented with the formula $AlR_mX_{3-m}$ wherein R is a linear or branched, $C_1$–$C_8$ alkyl group, or a mixture thereof, X is a halogen, preferably chlorine or bromine, and "m" is a decimal number between 1 and 3; followed by the addition to the composition thus obtained of at least one ionic compound of the type previously specified in such quantities that the ratio between B or Al and the atom M in the metallocene complex is within the range of 0.1 to 15, preferably from 1 to 6.

Examples of ionizing ionic compounds or multicomponent reactive systems capable of producing an ionic catalytic system by reaction with a metallocene complex of the present invention are described in the following patent publications, whose contents are incorporated herein as reference:

European patent applications, published with No.: EP-A 277.003, EP-A 277.004, EP-A 522.581, EP-A 495.375, EP-A 520.732, EP-A 478.913, EP-A 468.651, EP-A 427.697, EP-A 421.659, EP-A 418.044;

International patent applications published with No.: WO 92/00333, WO 92/05208; WO 91/09882.

U.S. Pat. No. 5,064,802, U.S. Pat. No. 2,827,446, U.S. Pat. No. 5,066,739.

Non-limiting examples of complex-cocatalyst combinations suitable for the preparation of the ionic catalytic systems of the present invention are schematized hereunder in table (1), with reference to the respective precursors from whose combination they can be obtained. Any compound of each column can be combined, if necessary, with any compound of the remaining columns, according to the method indicated.

TABLE 1

| Method | Metallocene (i) | Cocatalyst(ii) |
|---|---|---|
| ($m_1$) | o-BZD-[1-(3,5-dimethyl)Ind]$_2$ZrMe$_2$ | |
| | o-BZD-[1-(4,5,6,7-THInd)$_2$TiMe$_2$ | |
| | o-BZD-[1-(4,5,6,7-THInd)$_2$ZrMe$_2$ | [Ph$_3$C]$^+$ × [B(C$_6$F$_5$)$_4$]$^-$ |
| | o-BZD-[1-(3-methyl)Ind]$_2$HfH$_2$ | |
| | o-BZD-(1-Ind)$_2$ZrMe$_2$ | [Bu$_3$NH]$^+$ × [B(C$_6$F$_5$)$_4$]$^-$ |
| | o-BZD-(1-Ind)$_2$TiPr$^i_2$ | |
| | o-BZD-[1-(3,4,7-trimethyl)Ind]$_2$ZrH$_2$ | [PhNMe$_2$H]$^+$ × [B(C$_6$F$_5$)$_4$]$^-$ |
| | o-BZD-[1-(4,7-dimethyl)Ind]$_2$TiBz$_2$ | |
| | o-BZD-(Cp*)$_2$ZrMe$_2$ | |
| ($m_3$) | o-BZD-[1-(5,6-dimethyl)Ind]$_2$ZrCl$_2$ | |
| | o-BZD-[1-(4,7-dimethyl)Ind]$_2$TiBr$_2$ | |
| | 1,8-Naphth-(1-Ind)$_2$ZrCl$_2$ | [Ph$_3$C]$^+$ × [B(C$_6$F$_5$)$_4$]$^-$ |
| | 1,8-Naphth-(1-Ind)$_2$Zr(NMe$_2$)$_2$ | |
| | o-BZD-(Flu)$_2$ZrCl$_2$ | AlEt$_3$ |
| | o-BZD-[1-(3-methyl)Ind]$_2$HfCl$_2$ | |
| | o-BZD-[1-(3-methyl)Ind]$_2$TiCl$_2$ | [PhNMe$_2$H]$^+$ × [B(C$_6$F$_5$)$_4$]$^-$ |
| | o-BZD-(1-Ind)$_2$ZrCl$_2$ | |
| | o-BZD-(Flu)$_2$HfCl$_2$ | AlBu$^i_3$ |

TABLE 1-continued

| Method | Metallocene (i) | Cocatalyst(ii) |
|---|---|---|
| | o-BZD-(1-Ind)$_2$Ti(OCOCHEtBu)Cl | |
| | (Flu-o-BZD-Cp*)Ti(NMe$_2$)$_2$ | [Bu$_3$NH]$^+$ × [B(C$_6$F$_5$)$_4$]$^-$ |
| | o-BZD-[1-(4,5,6,7-THInd)$_2$TiCl$_2$ | |
| | o-BZD-[1-(4,7-dimethyl)Ind]$_2$TiCl$_2$ | |
| | o-BZD-(1-Ind)$_2$Zr[OCO(CH$_2$)$_5$C(Me)$_3$]$_2$ | |

Abbreviations: Me = methyl, Et = ethyl, Bu = n-butyl, Bu$^i$ = iso-butyl, Ph = phenyl, Bz = benzyl, Pr$^i$ = isopropyl, Ind = indenyl, THInd = 4,5,6,7-tetrahydroindenyl, Flu = fluorenyl, o-BZD = o-benzylidene.

Also included in the scope of the present invention are those catalysts which comprise two or more complexes having formula (I) mixed with each other. Catalysts of the present invention based on mixtures of complexes having different catalytic activities can be advantageously used in polymerization when a broader molecular weight distribution of the polyolefins thus produced, is desired.

According to another aspect of the present invention, in order to produce solid components for the formation of polymerization catalysts of olefins, the above complexes can also be supported on inert solids, preferably consisting of Si and/or Al oxides, such as, for example, silica, alumina or silico-aluminates. Known supporting techniques can be used for the supporting of these catalysts, which normally comprise contact, in a suitable inert liquid medium, between the carrier, possibly activated by heating to temperatures of over 200° C., and one or both of components (i) and (ii) of the catalyst of the present invention. It is not necessary, for the purposes of the present invention, for both components to be supported, as either the complex having formula (II) alone, or the organic compound B, al, Ga or Sn as defined above, may be present on the surface of the carrier. In the latter case the component which is not present on the surface is subsequently put in contact with the supported component, at the moment of the formation of the active polymerization catalyst.

The scope of the present invention also comprises complexes and catalytic systems based thereon, which have been supported on a solid by the functionalization of the latter and formation of a covalent bond between the solid and a metallocene complex included in the previous formula (II).

A particular method for forming a supported catalyst according to the present invention comprises pre-polymerizing a relatively small fraction of monomer or mixture of monomers in the presence of the catalyst, in order to include it in a solid microparticulate which is then fed to the reactor itself to complete the process in the presence of additional α-olefin. This enables a better control of the morphology and dimensions of the polymeric particulate obtained.

One or more other additives or components can be optionally added to the catalyst of the present invention, in addition to the two components (i) or (ii), to obtain a catalytic system suitable for satisfying specific requisites. The catalytic systems thus obtained are included in the scope of the present invention. Additives or components which can be used in the preparation and/or formulation of the catalyst of the present invention are inert solvents such as, for example, aliphatic and/or aromatic hydrocarbons, aliphatic and aromatic ethers, weakly coordinating additives (Lewis bases) selected, for example, from non-polymerizable olefins, ethers, tertiary amines and alcohols, halogenating agents such as silicon halides, halogenated hydrocarbons, preferably chlorinated, etc. and in addition all other possible components normally used in the art for the preparation of traditional homogeneous catalysts of the metallocene type for the (co)polymerization of ethylene and α-olefins.

Components (i) and (ii) form the catalyst of the present invention by contact with each other, preferably at temperatures ranging from room temperature to 60° C. and for times varying from 10 seconds to 1 hour, preferably from 30 seconds to 10 minutes.

The catalysts of the present invention can be used with excellent results in practically all known (co)-polymerization processes of α-olefins, both in continuous and batch, in one or more steps, such as, for example, processes at low (0.1–1.0 MPa), medium (1.0–10 MPa) or high (10–150 MPa) pressure, at temperatures ranging from 20 to 240° C., optionally in the presence of an inert diluent. Hydrogen can be conveniently used as molecular weight regulator.

These processes can be carried out in solution or suspension in a liquid diluent normally consisting of an aliphatic or cycloaliphatic saturated hydrocarbon having from 3 to 8 carbon atoms, but which may also consist of a monomer, as, for example, in the known copolymerization process of ethylene and propylene in liquid propylene. The quantity of catalyst introduced into the polymerization mixture is preferably selected so that the concentration of the metal M is between $10^{-5}$ and $10^{-8}$ moles/liter.

The polymerization can alternatively be carried out in gas phase, for example in a fluid-bed reactor, normally at pressures of 0.5 to 5 MPa and temperatures ranging from 50 to 150° C.

According to a particular aspect of the present invention, the catalyst for the (co)polymerization of ethylene and α-olefins is prepared separately (pre-formed) by contact of components (i) and (ii), and subsequently introduced into the polymerization environment. The catalyst can be introduced first into the polymerization reactor, followed by the reagent mixture containing the olefin or mixture of olefins to be polymerized, or the catalyst can be introduced into the reactor already containing the reagent mixture, or, finally, the reagent and the catalyst can be contemporaneously fed to the reactor.

According to another aspect of the present invention, the catalyst is formed in situ, for example by introducing components (i) and (ii) separately into the polymerization reactor containing the pre-selected olefinic monomers.

The catalysts of the present invention can be used with excellent results in the polymerization of ethylene to give linear polyethylene and in the copolymerization of ethylene with propylene or higher α-olefins, preferably having from 4 to 10 carbon atoms, to give copolymers with different characteristics in relation to the specific polymerization conditions and the quantity and structure of the α-olefin itself. Linear polyethylenes can be obtained, for example, with densities ranging from 0.880 to 0.940 and with molecular weights ranging from 10,000 to 2,000,000. The α-olefins preferably used as comonomers of ethylene in the production of low or medium density linear polyethylene (known with the abbreviations ULDPE, VLDPE and LLDPE according to the density), are 1-butene, 1-hexene and 1-octene.

The catalyst of the present invention can also be conveniently used in copolymerization processes of ethylene and propylene to give saturated elastomeric copolymers vulcanizable by means of peroxides and extremely resistant to aging and degradation, or in the terpolymerization of ethylene, propylene and a non-conjugated diene having from 5 to 20 carbon atoms, to obtain vulcanizable rubbers of the EPDM type. In the case of these latter processes, it has been observed that the catalysts of the present invention allow the production of polymers having a particularly high diene content and average molecular weight under the polymerization conditions.

For the preparation of EPDM, dienes which can be used for the preparation of these terpolymers are preferably selected from:

- dienes with a linear chain such as 1,4-hexadiene and 1,6-octadiene;
- branched dienes such as 5-methyl-1,4-hexadiene; 3,7-dimethyl-1,6-octadiene; 3,7-dimethyl-1,7-octadiene;
- dienes with a single ring such as 1,4-cyclohexadiene; 1,5-cyclo-octadiene; 1,5-cyclododecadiene;
- dienes endowed with bridged condensed rings such as dicyclopentadiene; bicyclo[2.2.1]hepta-2,5-diene; alkenyl, alkylidene, cycloalkenyl and cycloalkylidene norbornenes such as 5-methylene-2-norbornene, 5-ethylidene-2-norbornene (ENB), 5-propenyl-2-norbornene.

Among non-conjugated dienes typically used for preparing these copolymers, dienes containing at least one double bond in a tensioned ring are preferred, even more preferably 5-ethylidene-2-norbornene (ENB), and also 1,4-hexadiene and 1,6-octadiene.

In the case of EPDM terpolymers, the quantity of diene monomer does not exceed 15% by weight, and is preferably from 2 to 10% by weight. The propylene content on the other hand is conveniently between 20 and 50% by weight.

The catalysts of the present invention can also be used in homo- and co-polymerization processes of α-olefins of the known art, giving, with excellent yields, atactic, isotactic or syndiotactic polymers, depending on the structure and geometry of the metallocene complex having formula (II). α-olefins suitable for the purpose are those having from 3 to 20 carbon atoms, optionally also comprising halogens or aromatic nuclei such as, for example, propylene, 1-butene, 1-hexene, 4-methyl-1-pentene, 1-decene and styrene.

The present invention is further described by the following examples which, however, are purely illustrative and in no way limit the scope of the invention itself.

EXAMPLES

The analytical techniques and methods listed and briefly described hereunder were used in the following examples.

The characterization by means of $^1$H-NMR spectroscopy mentioned in the following examples, was carried out on a nuclear magnetic resonance spectrometer mod. Bruker-MSL-300, using $CDCl_3$ as solvent for each sample.

The molecular weight measurement of the olefinic polymers was effected by means of Gel-Permeation chromatography (GPC). The analyses of the samples were carried out in 1,2,4-trichloro-benzene (stabilized with Santonox) at 135° C. with a WATERS 150-CV chromatograph using a Waters differential refractometer as detector.

The chromatographic separation was obtained with a set of $\mu$-Styragel HT columns (Waters) of which three with pore dimensions of $10^3$, $10^4$, $10^5$ Å respectively, and two with pore dimensions of $10^6$ Å, establishing a flow-rate of the eluant of 1 ml/min.

The data were obtained and processed by means of Maxima 820 software version 3.30 (Millipore); the number (Mn) and weight (Mw) average molecular weight calculation was carried out by universal calibration, selecting polystyrene standards with molecular weights within the range of 6,500,000–2,000, for the calibration.

The determination of the structure by means of X-rays of the new complex of the present invention was effected on a Siemens AED diffractometer.

The mechanical properties of the products were determined by subjecting the copolymers to vulcanization. The corresponding method adopted for all these analyses together with the technique specified in technical literature, where available, are provided hereunder.

The determination of the content of units deriving from propylene and possible diene in the polymers is carried out (according to a method of the Applicant) by means of IR on the polymers in the form of films having a thickness of 0.2 mm, using an FTIR Perkin-Elmer spectrophotometer model 1760. The intensity of the characteristic peaks of propylene at 4390 $cm^{-1}$ and ENB at 1688 $cm^{-1}$ respectively, relating to the peak at 4255 $cm^{-1}$, is measured together with the quantity determined using a standard calibration curve.

The flow index (Melt Flow Index, MFI) of the polymers is determined in accordance with regulation ASTM D-1238 D.

The Mooney viscosity (1+4) is determined at 100° C. using a Monsanto "1500 S" viscometer, according to the method ASTM 1646/68.

As far as the mechanical properties are concerned, these analyses were effected on vulcanized polymers. (A) the vulcanization recipe and (B) the dynamo-mechanical determinations effected according to the methods indicated therein are specified below.

A) Vulcanization

Vulcanization mixtures were prepared using the formulation indicated in Table 2 below.

TABLE 2

| INGREDIENTS | PARTS BY WEIGHT |
| --- | --- |
| EPDM polymer | 100 |
| Carbon black FEF ® of the type "High Abrasion Furnace low structure" (CABOT) | 55 |
| Zinc oxide | 5 |
| Sulfur | 1.5 |
| Tetramethylthiuramdisulfide | 1.5 |
| Mercaptobenzothiazole | 0.75 |
| Paraffin oil EIL 570 ®, density 0.88 g/cc (EXXON) | 30 |

The mixture, homogenized on roll mixers, is vulcanized between press plates subjected to a pressure of 18 MPa and maintained at 165° C. for 40 minutes.

B) Mechanical characterization.

The mechanical characteristics of the vulcanized copolymers were determined on dumb-bell test-samples obtained from vulcanized plates.

The ultimate tensile strength measurement was effected according to the method ASTM D 412-68, the elongation to break according to the method ASTM D 412-68, the Shore A hardness according to the method ASTM D2240-68.

During the preparations of the examples the commercial reagents listed hereunder were used:
methyl-lithium (MeLi) 1.6 M in diethyl ether ALDRICH
butyl-lithium (BuLi) 2.5 M in hexane ALDRICH
zirconium tetrachloride ($ZrCl_4$) FLUKA
indene FLUKA
methylalumoxane (MAO) (Eurecene 5100 10T) WITCO 10% weight/volume of Al in toluene o-bromo-benzyl alcohol ALDRICH
2-methoxypropene ALDRICH
1-indanone ALDRICH The reagents and/or solvents adopted and not indicated above are those commonly used and are easily available at commercial operators specialized in the field.

Example 1

Synthesis of o-benzylidenebis-($^{5-1}$-indenyl)-zirconium dichloride

1) Synthesis of 1-(1-indenyl)-2-methylene-(1-indenyl)-benzene (formula VI)

0.4 ml of phosphorous oxychloride (POC$_{13}$) acting as catalyst are added to a mixture of 14 g of o-bromobenzyl alcohol (75 mmoles) and 72 ml of 2-methoxypropene (75 mmoles). The alcohol slowly dissolves. The mixture is left under stirring for two hours at room temperature. It is neutralized with triethylamine and dried obtaining about 20 g of an oily residue essentially consisting of 2-methoxy-2-(o-bromobenzyloxy)propane.

The residue is dilued with 150 ml of hexane and 30 ml of BuLi 2.5 M in hexane are added. A precipitate is formed. The mixture is left to rest for two hours, it is then filtered and washed with hexane, obtaining at the end the salt 2-[(1-methyl-1-methoxy)ethyloxymethyl]phenyl lithium.

10 g of 1-indanone (75 mmoles) dissolved in 50 ml of THF are added to the lithium salt dissolved in 100 of THF and cooled to −70° C. The mixture is left to rise to room temperature for a night. It is then poured into water, 50 ml of aqueous HCl 1:1 are added and the mixture is left under stirring for two hours. It is then extracted with ether and the extract is washed with bicarbonate until neutrality. Upon evaporation of the solvent and elution on a silica gel column using petroleum ether containing 10% of ethyl acetate, 7.6 g of spirobenzofuran derivative are obtained, having the following structural formula (VI):

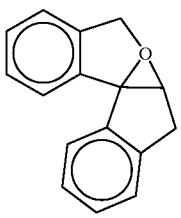

(VI)

Following the reaction scheme (I) herebelow, 6.5 g of spirofuran derivative (V) (29 mmoles) are suspended in 50 ml of aqueous HBr at 48% by weight and the mixture thus formed is kept under stirring for 50 hours at room temperature. It is then diluted with 10 ml of water and extracted with ethyl ether. The organic phase is separated, neutralized and dried by evaporation of the ether. The semisolid residue is purified by chromatography on a silica gel column, eluating with a mixture 9:1 of petroleum ether-methylene chloride. At the end, after evaporation of the eluant, 6.1 g of o-(1-indenyl)-benzyl bromide (21 mmoles) are isolated.

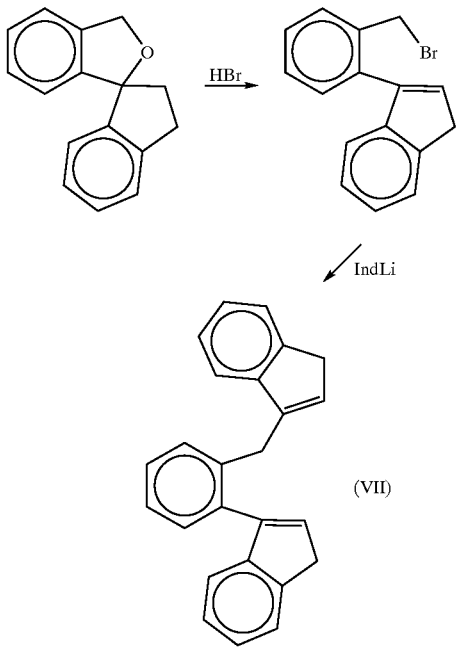

Reaction scheme (I)

8 ml of a 2.5 M solution of butyl lithium in hexane (20 mmoles) are added at room temperature to a solution of 4 g of indene (34 mmoles) in a mixture consisting of 100 ml of THF and 30 ml of hexane. The mixture is left under stirring for 4 hours and is then cooled to −80° C. 5.7 g of o-(1-indenyl)-benzyl bromide (20 mmoles) obtained as described above, are then added to the mixture and the temperature is left to rise to room temperature in about 2 hours. The mixture thus obtained is hydrolyzed and extracted with ethyl ether. The organic phase, after neutralization, drying and evaporation of the ether, leaves a residue which is purified by chromatography on a silica gel column, eluating with petroleum ether. At the end, after evaporation of the eluant, 5.7 g of a white solid are i obtained, which, after spectroscopic characterization, proves to be the desired product having formula (VII) (17 mmoles).

2) Synthesis of the zirconium complex (formula VIII)

1.74 grams of the compound having formula (VII), obtained as described above (5.44 mmoles), dissolved in 50 ml of anhydrous ethyl ether, are charged, under an atmosphere of argon, into a 100 ml tailed test-tube equipped with a magnetic stirrer. 8 ml of butyl lithium 1.6 M in hexane (12.8 mmoles) are added dropwise at room temperature to this light yellow-coloured solution and the mixture is kept under stirring for about 10 hours. At the end the reaction mixture takes on the form of a dark red solution. The volume of this solution is reduced to 10 ml, after which 30 ml of anhydrous n-hexane are added. A suspension is immediately formed which is then filtered; the solid is collected and subsequently washed with three 10 ml portions of n-hexane. The dilithium derivative of compound (VII) thus obtained is dried under vacuum (about 10 Pa) and is transferred, under an argon atmosphere, to a 100 ml tailed test-tube containing 50 ml of toluene, obtaining a suspension which is cooled to 0° C. 1.5 gr of ZrCl$_4$ (6.44 mmoles) are weighed separately and introduced, under argon, into the toluene suspension. After about 1 hour of stirring at 0° C., the temperature is left to rise to room temperature. The stirring is continued for a further 30 minutes, the mixture is then filtered on a porous septum and the mother liquor containing the desired complex is collected. The residue is washed again with toluene (3×10 ml) and the washing water is joined to the mother liquor. The limpid toluene solution thus obtained is left to rest for about two days at room temperature, with the formation of orange-coloured crystals. These are separated by filtration, washed with a small amound of toluene and characterized by NMR and X-rays. 0.82 g of the desired complex (formula VIII) are obtained, with a yield of 31% with respect to the quantity of initial ligand.

(VIII)

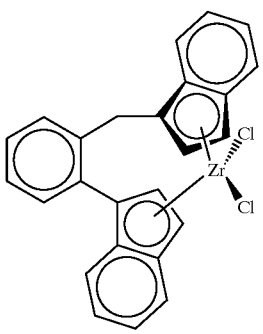

Figure 2:
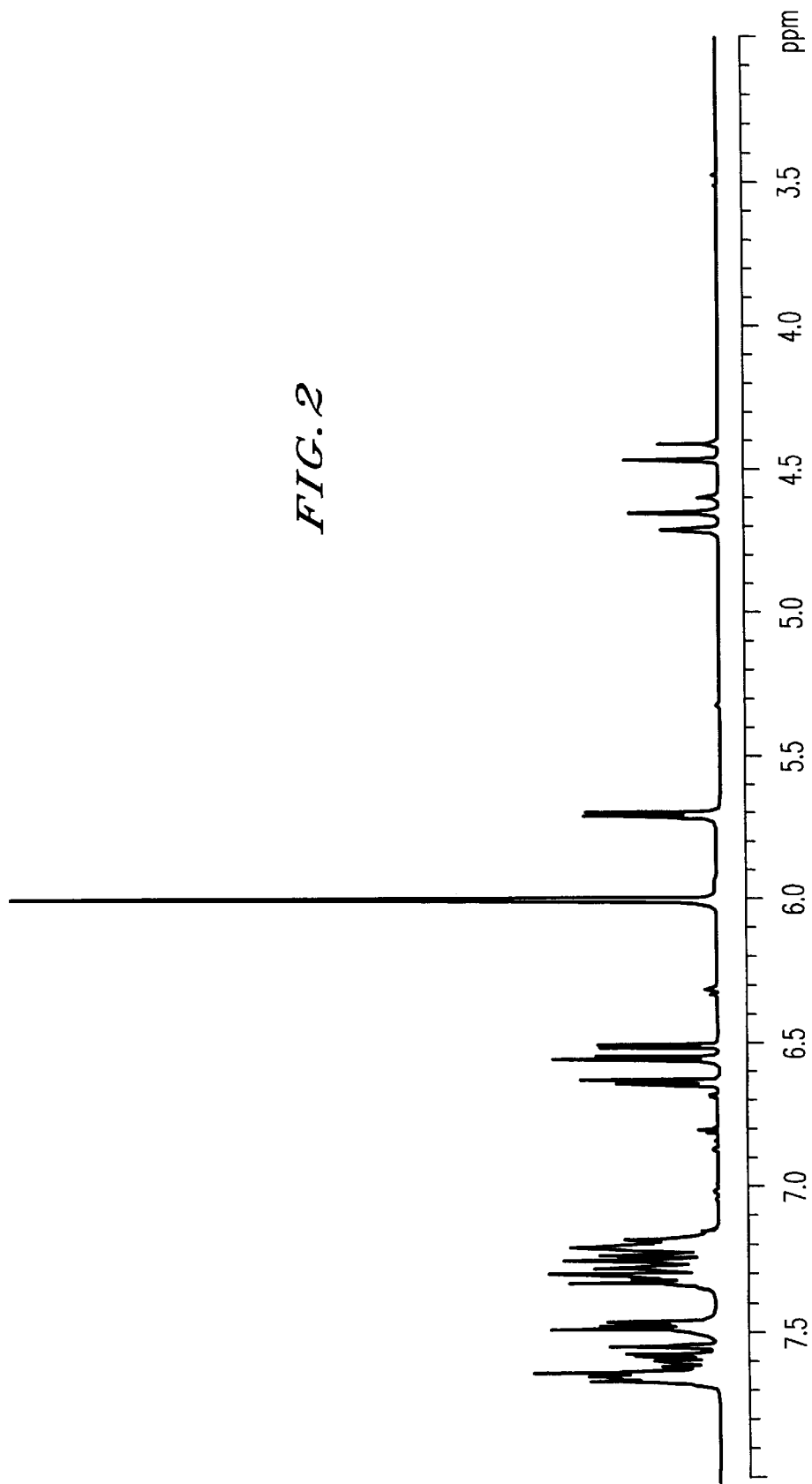
FIG. 2 is the $^1$H-NMR spectrum of the complex having formula (VIII)

The X-ray structure and $^1$H-NMR spectrum ($C_2D_2C_{14}$, δ ppm rel. to TMS) of the complex having formula (VIII) are indicated in FIGS. 1 and 2 respectively.

Example 2

Synthesis of o-benzylidenebis-(5,6-dimethyl-η$^{5-1}$-indenyl) zirconium dichloride 1) Synthesis of 5,6-dimethyl-1-indanone (Xa) and 5,6-dimethyl-indene (XIa)

A mixture of 69 g (0.543 moles) of 3-chloropropionyl chloride and 58 g (0.547 moles) of o-xylene are added in 1 hour to a solution of 164 g (1.23 moles) of $AlCl_3$ in 500 ml of nitromethane, maintained under argon, cooling with a water bath (25° C.). At the end of the addition, the mixture is kept under stirring for 5 hours. The reaction mass is then poured into 500 g of ice containing 100 ml of concentrated HCl. It is extracted with ethyl ether. The ether extracts are washed with HCl 2N and then with a saturated aqueous solution of NaCl until neutrality. They are then anhydrified with sodium sulfate and the solvent is evaporated obtaining 106.3 g of compound (IX) (98% yield).

(IX)

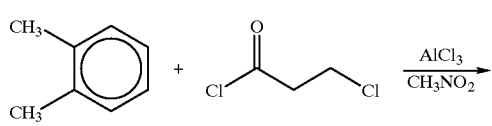

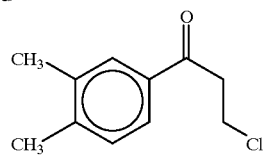

106.3 g of compound (IX) are slowly added to 420 ml of concentrated $H_2SO_4$. At the end of the addition the mixture is brought to 90° C., this temperature is maintained for 3 hours and the mixture is then poured onto ice. It is extracted with toluene. The organic extracts are washed with a saturated solution of $NaHCO_3$ and finally with a saturated solution of NaCl until neutrality. The solution is subsequently treated with activated carbon, filtered and dried on sodium sulfate. The residue obtained after evaporation of the solvent is recrystallized from petroleum ether to give 25 g (156 mmoles) of a 1:1 mixture of 5,6-dimethyl- and 6,7-dimethyl-1-indanone Xa and Xb (29% yield).

Xa

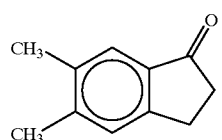

Xb

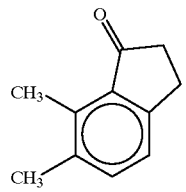

3.8 g (101 mmoles) of sodium boron hydride, are added in portions to the solution in THF of 25 g (156 mmoles) of the mixture of 1-indanones Xa and Xb obtained as described above, the mixture being maintained under an inert atmosphere at 10° C. At the end of the addition, the temperature is left to rise to room temperature and the mixture is stirred for 1 hour. The reaction mixture is then poured into water and ice and extracted with ethyl ether. A mixture containing both reduction products XIa and XIb indicated in the scheme below, is obtained. The ether extract is washed with water until neutrality and anhydrified on sodium sulfate. The residue obtained by evaporation of the solvent is recrystallized from petroleum ether giving 6.5 g of the single isomer 5,6-dimethyl-1-indanol (XIa) (26% yield).

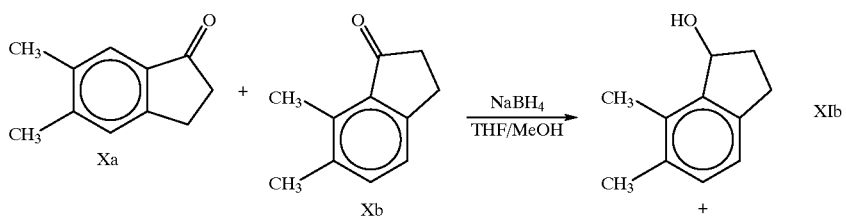

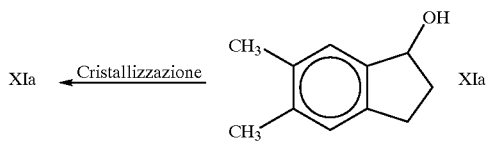

6.5 g (0.401 moles) of 5,6-dimethyl-1-indanol (XIa), 10 g of silica (MERCK), 70 ml of toluene and 70 ml of heptane are charged and mixed in a Markusson apparatus and reflux heated, azeotropically removing the water formed. After 16 hours the reaction is complete. The mixture is filtered, diluted with ethyl ether, washed with water and the organic phase is dried on sodium sulfate. After evaporation of the solvent, 5.2 g of 5,6-dimethyl-indene are obtained (90% yield).

2) Synthesis of 1-(5,6-dimethyl-1-indenyl)-2-(5,6-dimethyl-1-indenyl)methyl benzene (XIV)

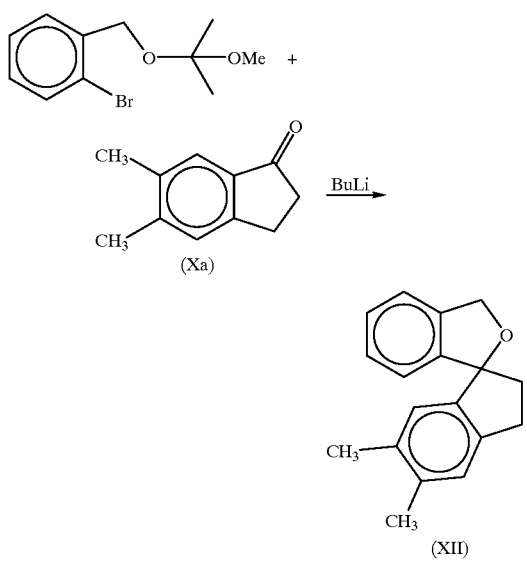

Reaction scheme (II)

27 ml (0.067 moles) of n-BuLi 2.5 M in hexane are added to a solution of 18.2 g (0.07 moles) of 2-methoxy-2-(o-bromobenzyloxy)propane, obtained as described above in example 1, paragraph 1, in 120 ml of hexane. The mixture is left under stirring for 2 hours and the hexane solution is then decanted. The solid residue is washed again with hexane by decanting and then dissolved in THF.

The mixture is cooled to −80° C. and a solution of 11.0 g (0.068 moles) of 4,7-dimethyl-1-indanone (formula Xa) dissolved in 30 ml of THF is added. The temperature is left to rise to room temperature for a night, and the mixture is then poured into water and ice to which 50 ml of HCl 1:1 are added. The mixture is maintained under stirring at 0° C. for 2 hours. It is extracted with ethyl ether and is subsequently washed until neutrality first with a saturated solution of NaHCO₃, then with water. After anhydrification of the organic phase on sodium sulfate, the solvent is evaporated. The residue is purified by chromatography on a silica gel column eluating with a mixture of hexane: ethyl acetate 9:1. After evaporation of the eluant 7.0 g (0.028 moles) of spirofuran derivative having formula (XII) are collected (see scheme II, 42% yield).

The above spirofuran derivative is put in 48 ml of HBr at 48% and the reaction mass is maintained at reflux tempera- ture for 16 hours. At the end, after dilution with water, it is extracted with ethyl ether, and the ether phase is washed with a saturated solution of sodium bicarbonate and then with water until neutrality. After anhydrification of the organic phase on sodium sulfate and evaporation of the solvent is evaporated, the residue obtained is purified by chromatography on a silica gel column eluating with a mixture of hexane:ethyl acetate in a ratio 9:1. 5.3 g (0.0168 moles) of o-[1-(5,6-dimethyl)-indenyl]-benzyl bromide (formula XIII, scheme III, 60% yield) are thus obtained.

14.4 ml (36.1 mmoles) of n-BuLi 2.5 M in hexane are added to 5.2 g (0.0388 moles) of 5,6-dimethylindene, obtained as described above (formula XIa), dissolved in a mixture of 100 ml of THF and 50 ml of hexane. 2 hours after completion of the addition the mixture is cooled to −70° C. and 5.3 g (0.0168 moles of o-[1-(5,6 dimethyl)-indenyl]-benzyl bromide (formula XIII) dissolved in 50 ml of THF are added. At the end of the addition the mixture is brought to room temperature and is left under stirring for 3 hours. It is poured into water slightly acidified with HCl and is then extracted with ethyl ether. The organic phase is neutralized by washings with water, anhydrified on sodium sulfate and the solvent is then evaporated. Upon purification of the residue on a silica gel column using petroleum ether as eluant, 60 9 of a solid are obtained, which after spectro- scopic characterization, proved to the desired ligand: 1-(5,6-dimethyl-1-indenyl)-2-(5,6-dimethyl-1-indenyl)methyl benzene (XIV).

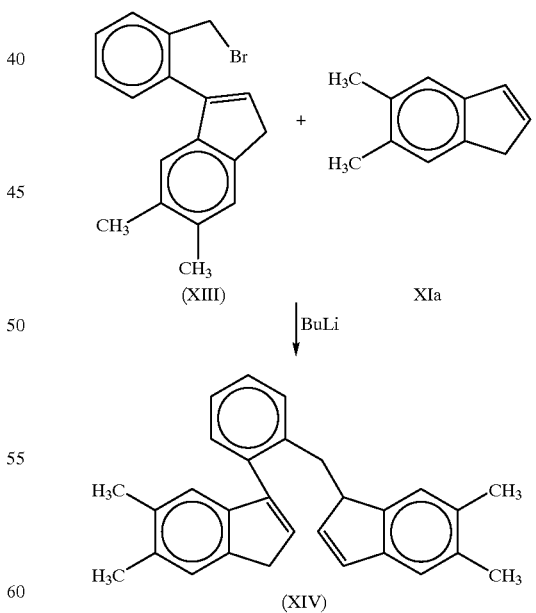

Reaction scheme (III)

3) Synthesis of the zirconium complex

The same procedure is adopted as described in paragraph 2 of example 1, reacting the same molar quantities of the bis-indenyl ligand and zirconium tetrachloride, under the same process conditions. 1.95 grams of compound having formula (XIV) (5.2 mmoles) are therefore reacted with 7.5 ml of a solution of lithium butyl, and subsequently with 1.45 g of ZrCl$_4$ to obtain at the end 0.8 g of the desired complex having the following formula (XV).

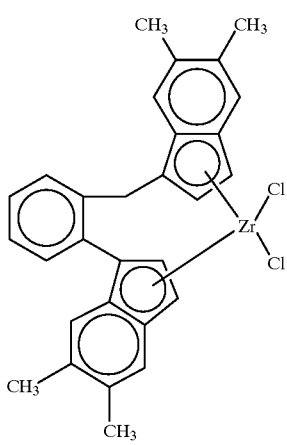

(XV)

Figure 3:
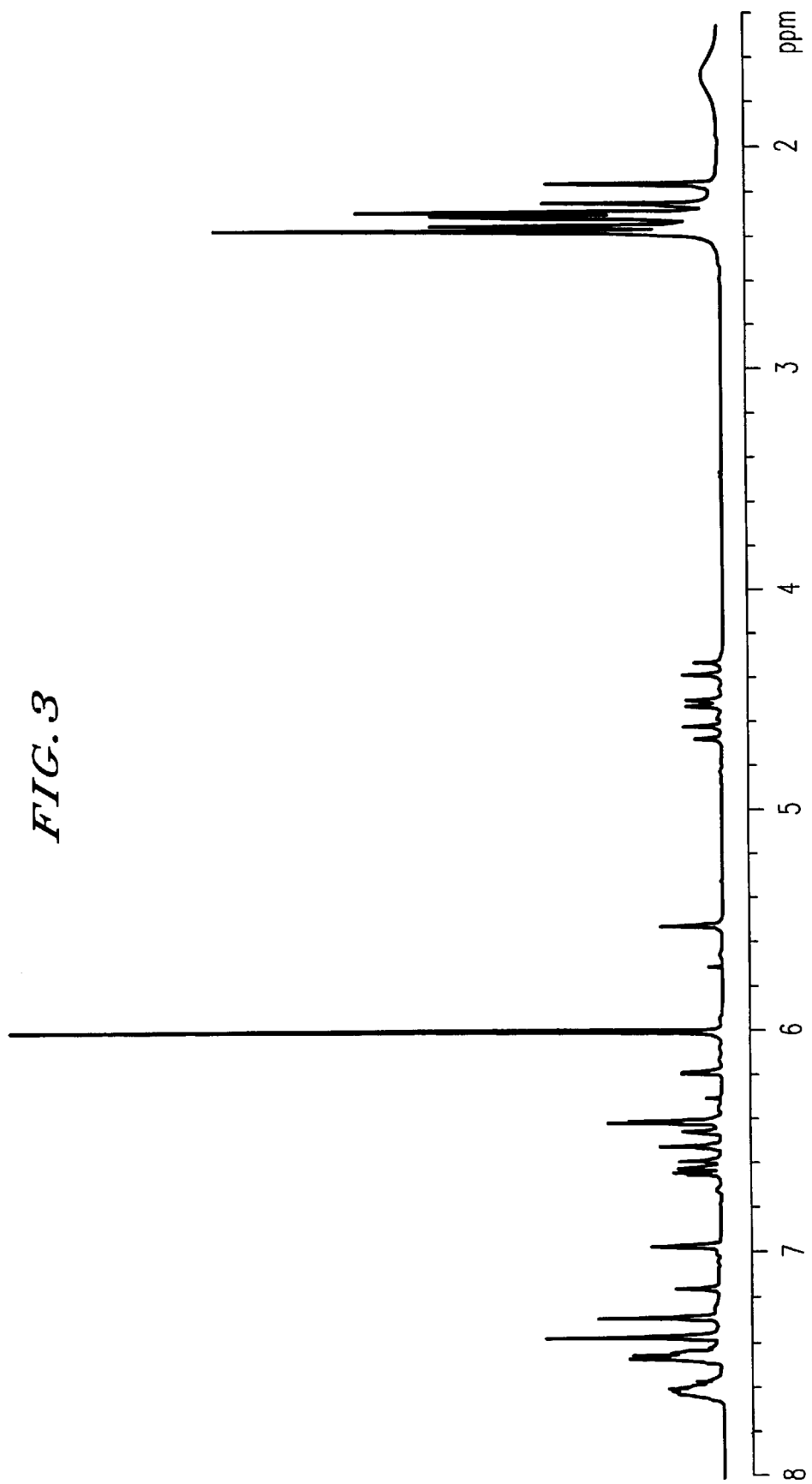
FIG. 3 is the $^1$H-NMR spectrum of the complex having formula (XV)

FIG. 3 indicates the $^1$H-NMR spectrum (C$_2$D$_2$Cl$_4$, δ ppm rel. to TMS) of the complex having formula (XV).

Example 3

Synthesis of o-benzylidenebis-(4,7-dimethyl-η$^{5-1}$-indenyl) zirconium dichloride 1) Synthesis of 4,7-dimethyl-1-indanone (XVII) and 4,7-dimethyl-indene (XVIII)

The procedure indicated in scheme (IV) is followed. A solution of 10 ml of 3-chloro propionyl chloride in 14.5 g (0.136 moles) of p-xylene is added dropwise in about 1 hour to a suspension of 16 g (0.120 moles) of AlCl$_3$ in 70 ml of methylene chloride, maintained at 0° C. in an inert atmosphere. At the end of the dripping, the temperature is left to rise to 10° C. and is maintained at 10–20° C. for about 2 hours. The reaction mixture is poured into ice and is extracted with methylene chloride. The organic extracts are washed with water until neutrality and the organic phase, after separation, is anhydrified on sodium sulfate. After evaporation of the solvent, a residue is obtained, essentially consisting of the compound having formula (XVI) indicated in the following scheme (IV).

The above residue is added to 90 ml of concentrated H$_2$SO$_4$ at such a rate as to maintain the temperatre at a value ranging from 20 to 30° C. At the end of the addition, the temperature is brought to 80° C. and the mixture is maintained under stirring for 2 hours. It is then poured into ice and is extracted with ethyl ether. The ether solution is washed until neutrality with a saturated solution of sodium bicarbonate and then water and is finally anhydrified on sodium sulfate. The solid obtained by evaporation of the ether is washed with petroleum ether and dried. 20 g of 4,7-dimethyl-1-indanone (formula XVII in scheme IV herebelow, 91% yield in the two passages) are thus obtained.

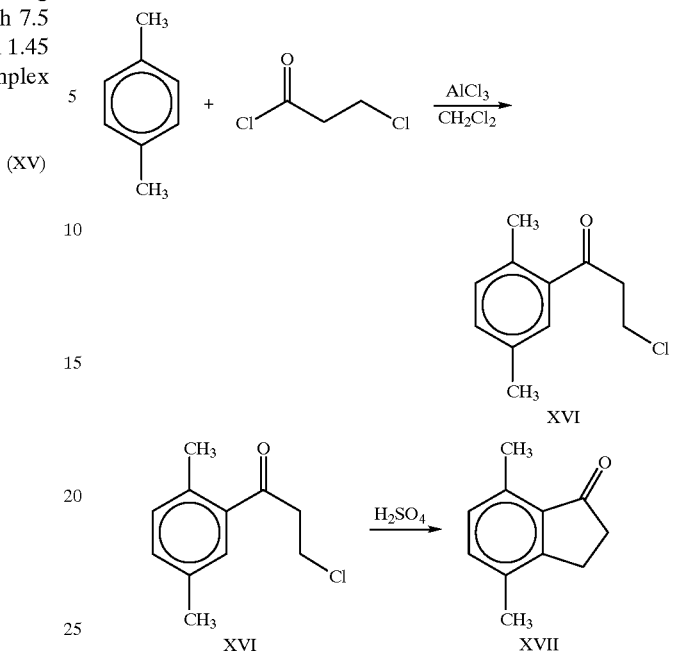

Reaction scheme (IV)

2.9 g (0.0181 moles) of 4,7-dimethyl-1-indanone (formula XVII) obtained as described above, are slowly added to a suspension of 0.350 g (0.0692 moles) of LiAlH$_4$ in 30 ml of ethyl ether, maintained at –30° C. in an inert atmosphere. The reaction is complete after 30 minutes. Ice and HCl 2N are cautiously added until acidification, the mixture is then extracted with ethyl ether, and the organic phase is subsequently separated and washed until neutrality. It is anhydrified on sodium sulfate and evaporated, obtaining a residue essentially consisting of 4,7-dimethyl-1-indanol. The residue is dissolved in 10 ml of THF, a pinch of p-toluenesulfonic acid is added and the mixture is brought to reflux temperature for 1 hour. Solid NaHCO$_3$ and Na$_2$SO$_4$ are then added. The mixture is filtered and the solvent evaporated obtaining 2.4 g of 4,7-dimethylindene (XVIII) (91% yield).

2) Synthesis of 1-(4,7-dimethyl-1-indenyl)-2-(4,7-dimethyl-1-indenyl)methyl benzene (XXI)

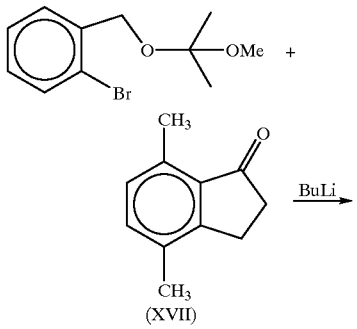

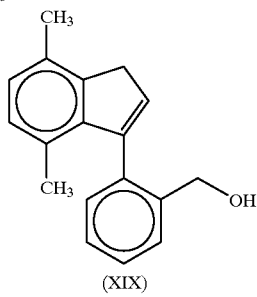

(XIX)

Reaction scheme (V)

30 ml of n-BuLi 2.5 M in hexane (75 mmoles) are added to 20 g of 2-methoxy-2-(o-bromobenzyloxy)propane (77.22 mmoles) obtained as in example 1.1, in a solution of 150 ml of hexane. At the end of the addition the mixture is left under stirring for 2 hours. The precipitation of the corresponding lithium salt takes place, as previously described in example 1. The hexane is decanted and the solid is again washed with hexane and then dissolved in 100 ml of THF. The mixture is cooled to −70° C. and 12.12 g (75.75 mmoles) of 4,7-dimethyl-1-indanone obtained as described above, dissolved in a sufficient quantity of THF, are then added slowly. The temperature is left to rise to room temperature for a night, the reaction mass is poured into ice, acidified with 50 ml of aqueous HCl 1/1 and left under stirring for 2 hours. It is extracted with ethyl ether, the organic phase is washed until neutrality with a solution of sodium bicarbonate and water, and is anhydrified on sodium sulfate. After evaporation of the solvent the residue is purified by chromatography on a silica gel column, eluting with a mixture of hexane/ethyl acetate 9:1. After evaporation of the eluant, 10 g of the alcohol having formula (XIX) are obtained (scheme V; 53% yield).

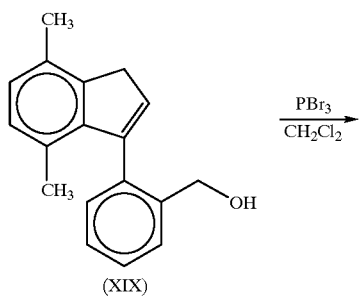

(XIX)

(XX)

Reaction scheme (VI)

Small portions of PBr$_3$ are added to a solution of 6.0 g of the alcohol having formula (XIX) (24 mmoles) in 50 ml of methylene chloride, maintained at 0° C., and the reaction trend is controlled by thin layer chromatography (TLC), until the disappearance of the alcohol. At the end, a saturated solution of NaHCO$_3$ is added dropwise, at 0° C. The mixture is then extracted with 100 ml of methylene chloride and the extracts are washed until neutrality. The residue obtained after anhydrification and evaporation of the solvent, is purified by silica gel chromatography eluating with a mixture of hexane/ethyl acetate 9:1. After evaporation of the eluant 4.0 g of the brominated compound having formula (XX) in scheme (VI) are obtained (52% yield).

4.12 ml (10.3 mmoles) of n-BuLi 2.5 M in hexane are added to a solution of 1.48 g of 4,7-dimethyl indene (XVIII) (10.3 mmoles; obtained as described above) in 55 ml of a mixture of THF-hexane 2/1. At the end of the addition, the mixture is left under stirring for 1 hour. It is then cooled to −70° C. and a solution of 2.3 g of the brominated compound having formula (XX) (7.37 mmoles) in THF/hexane are added dropwise. The mixture is left to rise to room temperature and is left to rest for 6 hours. It is then poured into water and is extracted with ethyl ether. The organic phase is washed until neutrality and dehydrated on sodium sulfate. The residue obtained by evaporation of the solvent is purified by silica gel chromatography eluating with petroleum ether. After evaporation of the eluant 2.0 g of the bis-indenyl ligand having formula (XXI) and indicated below, are obtained (72% yield).

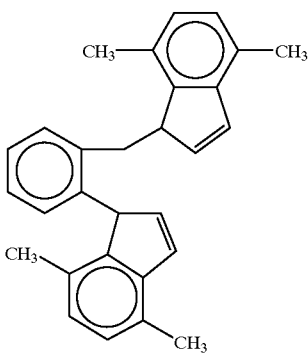

(XXI)

3) Synthesis of the zirconium complex (formula XXII)

The same procedure is adopted as described in paragraph 2 of example 1, reacting the same molar quantities of bis-indenyl ligand and zirconium tetrachloride, under the same process conditions. 1.95 grams of the compound having formula (XXI) (5.2 mmoles) are therefore reacted with 7.5 ml of a solution of lithium butyl, and subsequently with 1.45 g of ZrCl$_4$ obtaining at the end 0.9 g of the desired complex having the following formula (XXII).

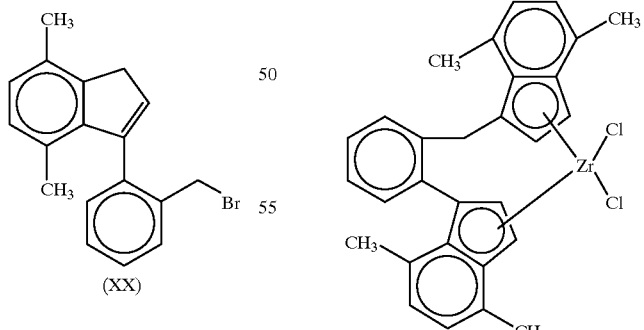

(XXII)

Figure 4:
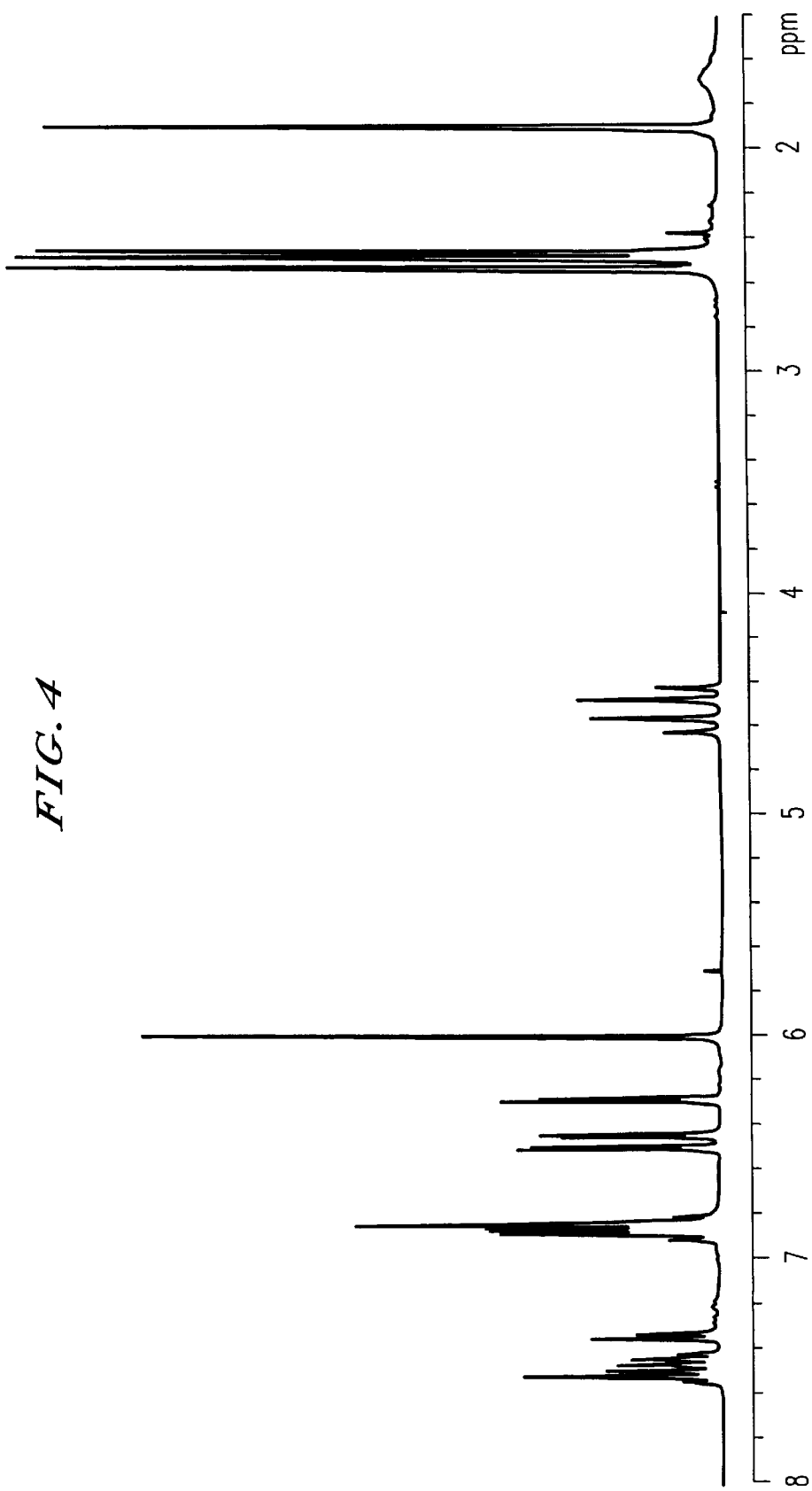
FIG. 4 is the $^1$H-NMR spectrum of the complex having formula (XXII).

FIG. 4 indicates the $^1$H-NMR spectrum (C$_2$D$_2$Cl$_4$, δ ppm rel. to TMS) of the complex having formula (XXII).

Examples 4–9

Terpolymerization of ethylene/prooylene/ethylidenenorbornene

Examples 4 to 9 refer to a series of terpolymerization tests for the preparation of an elastomeric copolymer of the EPDM type based on ethylene/propylene/ethylidenenorbornene, carried out using a preformed catalytic system comprising on the one hand the metallocene complex o-benzylidenebis-($\eta^{5-1}$-indenyl)-zirconium dichloride, obtained as described previously in example 1, and on the other hand methylalumoxane (MAO) as cocatalyst. The specific polymerization conditions of each example and the results obtained are indicated in Table 3 below, which provides, in succession, the reference example number, the quantity of zirconium used, the atomic ratio between aluminum in the MAO and zirconium, the polymerization pressure, the initial molar concentration of ethylidenenorbornene (ENB) in the liquid propylene, the activity of the catalytic system with reference to zirconium, the relative quantity, by weight, of the $C_2$, $C_3$ monomeric units and ENB in the polymer, the weight average molecular weight Mw and Mw/Mn molecular weight dispersion.

The polymerization is carried out in an 0.5 liter pressure reactor, thermostat-regulated and equipped with a magnetic drag stirrer. The reactor is previously flushed in the normal way, by washing with a dilute solution of MAO in toluene (about 0.1 M in Al) and drying under vacuum (0.1 Pascal for several hours).

120 g of "polymerization grade" liquid propylene are charged, at room temperature, into the reactor together with the necessary quantity of ENB for reaching the desired concentration. The reactor is then brought to a polymerization temperature of 40° C. and gaseous ethylene is introduced by means of a plunged pipe until the desired equilibrium pressure (22–28 ate) of the liquid mixture maintained under light stirring, is reached. Under these conditions, the molar concentration of ethylene in the liquid phase is between 12 and 24%, depending on the total pressure of the system, as can be easily calculated using the appropriate liquid-vapour equilibrium tables.

10 ml of toluene are charged into a suitable tailed test-tube, maintained under nitrogen and components (i) and (ii) are added in the appropriate quantities for the preparation of the desired catalytic composition. In particular, the desired quantity of the above metallocene complex is introduced as a toluene solution approximately $1 \times 10^{-3}$ molar and the MAO is then added as a solution 1.5 molar (as Al) in toluene (commercial product Eurecene 5100 10T of Witco), in such a quantity that the molar ratio aluminum/zirconium in the resulting catalytic mixture is between 3700 and 4000, as specified in Table 3. The catalyst solution thus formed is maintained at room temperature for a few minutes and is then poured under a stream of inert gas into a metal container from which it is transferred to the reactor, by an overpressure of nitrogen.

The polymerization reaction is carried out at 40° C., care being taken that the pressure is kept constant by continuously feeding ethylene to compensate the reacted part. After five minutes, the feeding of ethylene is interrupted, the monomers are degassed and the polymer is recovered after devolatilization of the monomers still present at 60° C. under vacuum (about 1000 Pa). The solid thus obtained is weighed and the activity of the catalyst is calculated as kilograms of polymer per gram of metal zirconium per hour ($Kg_{pol.}/g_{Zr} \cdot h$). The weight $M_w$ and number $M_n$ average molecular weight is measured on the dried, homogenized solid, together with the content of the various $C_3$ monomeric units (propylene) and ENB, using the known methods based on IR spectroscopy. The results are indicated in Table 3.

TABLE 3

Ethylene/propylene/ethylidenenorbornene copolymerization

| Example Nr. | Catalyst | | $P_{total}$ | $ENB_{feed}$ | Activity | $C3_{pol.}$ | $ENB_{feed}$ | Mw | Mw/Mn |
| --- | --- | --- | --- | --- | --- | --- | --- | --- | --- |
| | Zr mol. × $10^6$ | Al/Zr | (MPa) | (moles %) | ($kg_{pol}/g_{Zr}$ × h) | (weight %) | (weight %) | | |
| 4 | 0.6 | 3850 | 25 | 0.4 | 4850 | 38.3 | 2.7 | 380.000 | 2.6 |
| 5 | 0.6 | 3850 | 25 | 0.8 | 3310 | 36.5 | 4.1 | 260.000 | 3.0 |
| 6 | 1.2 | 3850 | 25 | 1.6 | 1770 | 37.6 | 7.4 | 262.000 | 2.8 |
| 7 | 0.7 | 3750 | 25 | 1.6 | 2180 | 34.5 | 7.3 | 344.000 | 2.4 |
| 8 | 1.2 | 3900 | 22 | 1.6 | 1300 | 48.3 | 10.1 | 235.000 | 2.4 |
| 9 | 0.6 | 3750 | 28 | 1.6 | 2680 | 33.9 | 6.5 | 572.000 | 3.7 |

Examples 10–14

Copolymerization of ethylene/propylene and terpolymerization with ENB

Ethylene/propylene copolymerization tests and terpolymerization tests with ENB were carried out, using the same preformed catalytic system as the previous examples 4 to 9. The specific polymerization conditions of each example and the results obtained are indicated in Table 4 below, which provides, in succession, the reference example number, the quantity of zirconium used, the atomic ratio between aluminum in the MAO and zirconium, the polymerization pressure, the initial molar concentration of ethylidenenorbornene (ENB) in the liquid propylene, the quantity of hydrogen initially introduced, the activity of the catalytic system with reference to zirconium, the relative quantity, in moles, of the $C_2$, $C_3$ monomeric units and ENB in the polymer, the MOONEY viscosity of the polymer measured at 100° C., and the mechanical characteristics of the polymer (only for EPDM) after vulcanization (ultimate tensile strength C.R.; elongation to break A.R., Shore A hardness at 160° C.).

The polymerization is carried out in a 3 liter pressure reactor, thermostat-regulated and equipped with a magnetic drag stirrer. The reactor is flushed by washing with about 500 g of liquid propylene, containing about 2 g of aluminum triisobutyl (TIBA). The mixture is discharged, and the reactor washed again with a small amount of fresh propylene and then emptied.

About 800 g of "polymerization grade" liquid propylene are charged into the reactor together with the necessary quantity of ENB for reaching the desired concentration, and about 1 ml of an 0.3 molar solution of TIBA in hexane, whose sole purpose is to act as scavenger, is then introduced. A small quantity of hydrogen is optionally added as molecular weight regulator. The reactor is brought to a polymerization temperature of 45° C. and gaseous ethylene is introduced by means of a plunged pipe until the desired equilibrium pressure (22–28 ate) of the liquid mixture maintained under light stirring, is reached. Under these conditions, the molar concentration of ethylene in the liquid phase is about 12–20%, depending on the total pressure of the system.

10 ml of toluene are charged into a suitable tailed test-tube, maintained under nitrogen and components (i) and (ii) are added in the appropriate quantities for the preparation of the desired catalytic composition. In particular, the desired quantity of the above metallocene complex, obtained as described in example 1, is introduced as a toluene solution approximately $10^{-3}$ molar and the MAO is then added in such a quantity that the molar ratio aluminum/zirconium in the resulting catalytic mixture is between 6000 and 7000, as specified in Table 4. The catalyst solution thus formed is maintained at room temperature for a few minutes and is then poured under a stream of inert gas into a metal container from which it is transferred to the reactor, by an overpressure of nitrogen. The polymerization reaction is carried out at 45° C., care being taken that the pressure is kept constant by continuously feeding ethylene to compensate the reacted part. After 1 hour, the feeding of ethylene is interrupted, the residual monomers are degassed and the autoclave is rapidly cooled to room temperature. The polymer is recovered and the devolatilization of the monomers is completed by calendering at about 80° C. The solid copolymer thus obtained is weighed and the activity of the catalyst is calculated as kilograms of polymer per gram of metal zirconium per hour ($Kg_{pol.}/g_{Zr} \cdot h$).

These copolymers are characterized by the content of monomeric units determined by IR spectroscopy and various mechanical properties measured after vulcanization with the method described above. The characterization results and polymerization conditions are indicated in Table 4 below.

The examples demonstrate that the catalytic systems obtained starting from the metallocene complexes of the present invention are active for the production of ethylene-propylene elastomeric copolymers and ethylene-propylene-diene terpolymers with a high Mooney viscosity.

Example 15: (comparative)

A polymerization test was carried out adopting the same equipment and with the same procedure as the previous example 10, but using the complex 1,2-ethylenebis($\eta^5$-1-indenyl)zirconium dichloride (WITCO commercial product), as component of the catalytic system instead of the complex o-benzylidenebis($\eta^5$-1-indenyl)zirconium dichloride of the present invention, and under the process conditions specified in Table 4 below. The copolymers thus obtained were characterized as described above and the results obtained are summarized in Table 4 below.

TABLE 4

Ethylene copolymerization and terpolymerization

| Example Nr. | Catalyst Zr mol. × $10^6$ | Al/Zr | $P_{total}$ (MPa) | $ENB_{feed}$ (moles %) | Total $H_2$ (mmoles) | Activity ($kg_{pol}/g_{Zr} \times h$) | $C3_{pol.}$ (weight %) | $ENB_{feed}$ (weight %) | MOONEY (ML4 + 100) | C.R (kg/cm$^2$) | A.R. (%) | Shore A (minutes) |
|---|---|---|---|---|---|---|---|---|---|---|---|---|
| 10 | 0.13 | 7200 | 24 | — | 0.45 | 7700 | 45 | — | 65($^3$) | — | — | — |
| 11 | 0.21 | 6900 | 24 | 0.4 | 0.45 | 5760 | 45 | 3.0 | 85 | 101 | 380 | 59 |
| 12 | 0.24 | 6700 | 24 | 0.5 | 0.45 | 5560 | 42 | 3.0 | 95 | n.m. | n.m. | n.m. |
| 13 | 0.43 | 6100 | 24 | 0.8 | 0.45 | 3270 | 43 | 4.0 | 84 | 104 | 325 | 60 |
| 14($^4$) | 0.70 | 6000 | 22 | 1.1 | 1.1 | 1600 | 28 | 8.5 | 92 | n.m. | n.m. | n.m. |
| 15($^{1,2}$) | 0.48 | 9000 | 23 | — | — | 2800 | 52 | — | <10 | — | — | — |

Notes:
($^1$)= comparative example; ($^2$)= Temperature 40° C.; ($^3$)= measured at 125° C.; ($^4$)= feed: 250 g propylene and 550 g propane; n.m. = not measured

Examples 16–19
copolymerization of ethylene/propylene and terpolymerization with ENB A series of co- and ter-polymerization ethylene/propylene/ENB tests is carried out in a 60 liter reactor equipped with a thermostat-regulated jacket with water circulation, a mechanical stirrer and a continuous feeding system of the monomers, connected by means of a valve at the bottom to a 600 liter stripper for the devolatilization of the polymer obtained. For a more effective temperature control, the reactor is additionally equipped with a special section which allows the extraction in continuous of a part of the vapour phase which is condensed and re-charged into the reactor as liquid.

The composition of the reaction mixture, maintained in liquid/vapour equilibrium, is determined with a frequency of 6 minutes by means of an automatic analysis system of the vapour phase with a COMBUSTION ENGINEERING process gas-chromatograph model 3100, equipped with a Chromosorb 102 60/80 column.

The monomers and propane are introduced into the reactor, thermostat-regulated at 45° C., up to a liquid volume of 35 liters, the respective quantities being regulated so that the composition of the vapour phase corresponds to that indicated in Table 5 below. Under these conditions the total pressure is normally between 1.5 and 2.0 MPa.

The catalyst is prepared separately, as a solution in toluene, by mixing the desired quantities of MAO (in toluene at 10% by weight) and o-benzylidenebis-($\eta^5$-1-indenyl)zirconium dichloride complex (0.1% weight/volume in toluene), in order to respect the proportions indicated in Table 5.

About 4.3 g (28 mmoles) of aluminumtriisobutyl in a solution of hexane (13% weight/volume) are introduced into the reactor, to act as scavenger. The mixture is kept under stirring for a few minutes and the catalyst solution is then introduced using a special container connected to the reactor and pressurized with anhydrous nitrogen.

The polymerization is then carried out for the duration of an hour, keeping the temperature constant at 45° C. and continuously feeding a further quantity of monomers so that the composition of the vapour in equilibrium with the liquid remains constant with the values specified in Table 5. At the end, the contents of the reactor are discharged into the stripper containing about 300 liters of water at room temperature and the residual monomers and propane are removed by evaporation. The remaining aqueous suspension is filtered, and the polymer obtained is dried in a calender and characterized. The results are indicated in Table 5.

TABLE 5

Ethylene copolimerization and terpolymerization

| Example Nr. | 16 | 17 | 18 | 19 |
|---|---|---|---|---|
| Catalyst millimoles Zr | 0.004 | 0.02 | 0.01 | 0.01 |
| Al/Zr | 5000 | 6000 | 6000 | 6000 |
| Ethylene (moles %) | 33.0 | 30.1 | 28.3 | 29.5 |
| Propylene (moles %) | 16.0 | 16.6 | 15.4 | 18.5 |
| Propane (moles %) | 51.0 | 53.2 | 54.0 | 47.1 |
| ENB$_{initial}$ (ml) | — | 150 | 150 | 250 |
| H$_2$ $_{initial}$ (mmoles) | 0.07 | 0.15 | 0.08 | 0.17 |
| Activity (kg$_{pol.}$/g$_{Zr}$ · h) | 1900 | 1000 | 1515 | 700 |
| C3$_{pol.}$ (weight %) | 27 | 31 | 29 | 27 |
| ENB$_{pol.}$ (weight %) | — | 3.7 | 3.5 | 7.6 |
| Intr. Viscos. (dl/g) | 1.6 | 1.4 | 2.0 | — |
| Mooney (ML 1 + 4) | 57 | 40 | 82([1]) | 31 |

([1]): measured at 125° C.

Example 20
copolymerization of ethylene/1-hexene
I) Preparation of the catalyst

A solution of the polymerization catalyst of the present invention is prepared separately by dissolving in 50 ml of anhydrous toluene, 23 mg (0.048 mmoles) of the complex having formula (VIII) prepared according to the previous example 1, and adding to this mixture, at room temperature, 3 ml of a solution of MAO at 10% by weight in toluene (titer of Al=1.57 M) in so that the atomic ratio Al/Zr is more or less equal to 100. The solution is matured by leaving it under stirring for 30 minutes at room temperature, before being introduced into the polymerization mixture.

II) Polymerization 900 ml of toluene (previously distilled on metallic sodium), 60 ml of 1-hexene (previously distilled on calcium hydride, CaH$_2$) and 1.5 ml of the above solution of MAO at 10% in toluene are charged into a BUCHI autoclave with a 2 liter glass reactor, equipped with a propeller stirrer and thermostat-regulated jacket, and maintained under vacuum for at least two hours during which three washings with nitrogen are effected. The autoclave is pressurized with ethylene at 0.2 MPa and heated to 40° C.

The autoclave is depressurized and 1.1 ml of the catalyst solution prepared as described above, are introduced, in a stream of ethylene, in such a way as to have an atomic ratio of 2500 between the zirconium in the complex and total aluminum contained in the MAO (resulting from the sum of that introduced with the catalyst solution and that introduced directly into the autoclave). The autoclave is brought again to a pressure of 2 ate with ethylene and the polymerization is carried out for 30 minutes, thermostat-regulating the temperature at 40° C. and continuously feeding ethylene to keep the pressure constant for the whole duration of the test. At the end, the reaction is interrupted by the addition of 5 ml of acidified methanol, the autoclave is depressurized and the polymer is recovered by precipitation with 3 liters of acidified methanol and subsequent washings with acetone. After drying, 15 g of an ethylene/1-hexene copolymer (LLDPE) are obtained, having the following characteristics:
number average molecular weight (Mn) 122,000 and weight average molecular weight (Mw) 327,000
molecular weight distribution (MWD=Mw/Mn): 2.7
monomeric units deriving from 1-hexene (1-hexene inserted): 8%
reactivity product of the monomers ($r_1 \cdot r_2$): 0.64
yield: 330 kg$_{POL}$/(g$_{Zr}$·h)

Example 21
copolymerization of ethylene/1-octene

A copolymerization test of ethylene/1-octene is carried out operating with exactly the same procedure and the same materials as the previous example 20, but using 75 ml of 1-octene instead of 60 ml of 1-hexene.

At the end, after drying, 11 g of an ethylene/1-octene copolymer (LLDPE) are obtained, having the following characteristics:
number average molecular weight (Mn) 164,000 and weight average molecular weight (Mw) 362,000
molecular weight distribution (MWD Mw/Mn): 2.2
monomeric units deriving from 1-octene (1-octene inserted): 7.3%
reactivity product of the monomers ($r_1 \cdot r_2$): 0.45
yield: 242 kg$_{POL}$/(g$_{Zr}$·h)

Example 22
high temperature polymerization

A polymerization test is carried out in a 1 liter adiabatic steel reactor, capable of operating up to about 100 MPa and at temperatures ranging from 160 to 220° C.

Two streams containing the monomers and the catalyst solution respectively, are fed to the reactor, the flow-rate being maintained at such a value as to allow a residence time of about 40 seconds. The conversion per passage, and consequently the temperature, is controlled and regulated by the flow-rate of the catalyst solution so as to maintain a polymer production within the range of 3–4 kg/h.

The catalyst solution is prepared by dissolving 550 mg (1.14 mmoles) of the complex o-benzylidenebis-($\eta^5$-1-indenyl)zirconium dichloride, prepared according to example 1 above, in 90 ml of toluene, and adding 150 ml of a solution of MAO in toluene (Al titer=4.5 M) (Al/Zr ratio=600). This solution is maintained under stirring at room temperature for about 1 hour, and then diluted by adding 1800 ml of Isopar-L before being introduced into the reactor. The concentration of Zr in the solution fed is 0.507 mM. The stream containing the monomers consists of 64% of ethylene by volume and 46% of 1-butene. The polymerization temperature is kept at a constant value of about 160° C. and the pressure is set at 80 MPa.

Under these conditions, an ethylene-butene copolymer (LLDPE) is obtained, having the following characteristics:

$M_n$=42,000; $M_w$=115,000; MWD=2.7;

(MFI)=0.42 g/10 min; density=0.9218 g/cm$^3$;

Number of short chain branchings=8.3/(1000 C)

Melting point=120.1° C.

The catalytic activity proved to be 9,200 kg$_{polymrer}$/g$_{Zr}$

Example 23
Catalyst in ionic form

The following products are introduced in order into a BUCHI type autoclave, with a 2 liter steel reactor, equipped with an anchor stirrer and thermostat-regulated jacket with liquid circulation, previously flushed and dried under vacuum (0.1 Pa) for at least two hours: 1 liter of heptane and 250 g of propylene. The mixture is heated to 50° C. and ethylene is introduced, under stirring, by means of a plunged pipe, until a total pressure of 1.3 MPa is reached.

1.0 ml of a 1.2 M solution of aluminum triisobutyl in toluene, and 4 ml of a 7.5–104 M solution of o-benzylidenebis-($\eta^5$-1-indenyl) zirconium dichloride obtained according to example 1 above, are introduced separately into an appropriate tailed test-tube, maintained under nitrogen. After keeping the solution under stirring for 15 minutes at room temperature, 3 ml of a $1.8 \cdot 10^{-3}$ M solution in toluene of triphenylcarbenium tetrakis-(pentafluorophenyl)borate $[Ph_3C]^+ \cdot [B(C_6F_5)_4]^-$ are added, and the solution obtained is immediately transferred to a suitable container situated above the autoclave, from which it is pushed into the reactor by pressurization with nitrogen. The polymerization starts almost immediately and continues for 30 minutes, the temperature being maintained at 50° C. and the pressure at 1.3 MPa by continuous feeding of ethylene. At the end, after degassing the residual monomers, the polymer is recovered by means of coagulation by adding 1 liter of methanol, filtration and subsequent drying. 90.5 g of an ethylene/propylene copolymer are thus obtained, having a content of propylene units of 26.9% by weight, an $M_n$ average molecular weight=100,000 and $M_w/M_n$ dispersion= 1.8. The activity of the catalyst was 332 $kg_{polymer}/g_{Zr}$.

What is claimed is:

1. A metallocene complex, which can be used in the formation of a catalyst for the (co)polymerization of ethylene and α-olefins, having the following formula(II):

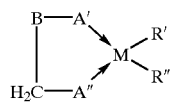

(II)

wherein: M represents a metal selected from titanium, zirconium or hafnium;

each A' or A" independently represents an organic group containing an $\eta^5$-cyclopentadienyl ring of an anionic nature, coordinated to the metal M;

each R' or R" independently represents a group of an anionic nature σ-bound to the metal M;

B represents an unsaturated divalent organic residue having from 1 to 30 carbon atoms, bound, respectively, to the ring of group A' and to the —CH$_2$— methylene group by means of unsaturated atoms different from hydrogen.

2. The complex according to claim 1, wherein at least one of the A' and A" groups, is selected from $\eta^5$-indenyl or $\eta^5$-(4,5,6,7-tetrahydro)indenyl.

3. The complex according to claim 1 wherein said metal M is zirconium.

4. The complex according to claim 1 wherein said divalent organic residue "B" is selected from ortho-phenylene groups having from 6 to 20 carbon atoms, or peri-naphthalene groups having from 10 to 20 carbon atoms.

5. The complex according to claim 1, wherein each of the R' or R" groups having formula (II) is independently selected from hydride, halide, a $C_1$–$C_{20}$ alkyl or alkylaryl group, a $C_3$–$C_{20}$ alkylsilyl group, a $C_5$–$C_{20}$ cycloalkyl group, a $C_6$–$C_{20}$ aryl or arylalkyl group, a $C_1$–$C_{20}$ alkoxyl or thioalkoxyl group, a $C_1$–$C_{20}$ carboxylate or carbamate group, a $C_2$–$C_{20}$ dialkylamide group and a $C_4$–$C_{20}$ alkylsilylamide group.

6. A catalyst for the (co)polymerization of ethylene and other α-olefins, comprising at least the two following components in contact with each other:
    (i) at least one metallocene complex according to claim 1, and
    (ii) a cocatalyst consisting of at least one organic compound of an element M' different from carbon and selected from the elements of groups 2, 12, 13 or 14 of the periodic table.

7. A catalyst for the (co)polymerization of ethylene and other α-olefins, comprising at least the two following components in contact with each other:
    (i) at least one metallocene complex according to claim 4, and
    (ii) a cocatalyst consisting of at least one organic compound of an element M' different from carbon and selected from the elements of groups 2, 12, 13 or 14 of the periodic table.

8. The catalyst according to claim 6 wherein said element M' in component (ii) is selected from boron, aluminum, zinc, magnesium, gallium and tin.

9. The catalyst according to claim 6, wherein said component (ii) is a polymeric aluminoxane.

10. The catalyst according to claim 9, wherein the atomic ratio between the metal M in the complex having formula (II) and Al in the aluminoxane is between 100 and 5000.

11. The catalyst according to claim 6 wherein said component (ii) consists of at least one compound or a mixture of organometallic compounds of M' capable of reacting with the complex having formula (II) extracting from this a σ-bound R' or R" group to form on the one hand at least one neutral compound, and on the other hand an ionic compound consisting of a metallocene cation containing the metal M and a non-coordinating organic anion containing the metal M', whose negative charge is delocalized on a multicentric structure.

12. The catalyst according to claim 11, wherein the atomic ratio between the metal M' in component (ii) and the metal M in component (i) is between 1 and 6.

13. The catalyst according to claim 11 wherein said component (ii) consists of an ionic-ionizing compound selected from the group of compounds having one of the following formulae:

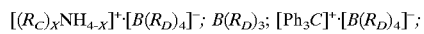

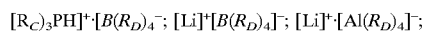

wherein the subscript "x" is an integer between 0 and 3;

each $R_C$ group independently represents an alkyl or aryl radical having from 1 to 10 carbon atoms and each $R_D$ group independently represents an aryl radical partially or totally fluorinated, having from 6 to 20 carbon atoms.

14. The catalyst according to claim 13, wherein said component (ii) comprises, in addition to said ionic-ionizing compound, an aluminum alkyl having the formula $AlR_mX_{3-m}$, wherein R is a linear or branched, $C_1$–$C_8$ alkyl group, X is chlorine or bromine, and "m" is a decimal number between 1 and 3, with a ratio between B or Al in the ionic-ionizing compound and Al in the aluminum alkyl ranging from 100/1 and 500/1.

15. A process for the (co)polymerization of ethylene or α-olefins, both in continuous and batch, in one or more steps, at low (0.1–1.0 MPa), medium (1.0–10 MPa) or high (10–150 MPa) pressure, at a temperature ranging from 20 to 240° C., optionally in the presence of an inert diluent, characterized in that at least ethylene or at least one α-olefin is put in contact, under one of the above conditions, with a catalyst according to claim 6.

16. The process according to claim 15, wherein ethylene is copolymerized with at least one α-olefin having from 3 to 10 carbon atoms.

17. The process according to claim 16, wherein, in addition to at least one c-olefin, an aliphatic or alicyclic, non-conjugated diene having from 5 to 20 carbon atoms, is copolymerized with ethylene.

18. The process according to claim 15, characterized in that it is carried out in solution or suspension in a suitable inert liquid medium consisting of an aliphatic or cycloaliphatic hydrocarbon having from 3 to 15 carbon atoms, or a mixture of these.

19. The process according to claim 15 characterized in that it is carried out without an inert diluent.

20. The process according to claim 15, characterized in that the concentration of the metal M having formula (II) in the polymerization mixture is between $10^{-5}$ and $10^{-8}$ moles/liter.

* * * * *